United States Patent
Darcy et al.

(10) Patent No.: US 11,964,059 B2
(45) Date of Patent: *Apr. 23, 2024

(54) METHODS OF DELIVERING AN ORAL CARE ACTIVE BY ADMINISTERING ORAL CARE ARTICLES COMPRISING A FILAMENT

(71) Applicant: The Procter & Gamble Company, Cincinnati, OH (US)

(72) Inventors: Trevor John Darcy, Cincinnati, OH (US); Steven Ray Gilbert, Fairfield, OH (US); Gregory Charles Gordon, Loveland, OH (US); Rajeev Chhabra, Mason, OH (US); William Maxwell Allen, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 598 days.

This patent is subject to a terminal disclaimer.

(21) Appl. No.: 17/141,562

(22) Filed: Jan. 5, 2021

(65) Prior Publication Data

US 2021/0154150 A1 May 27, 2021

Related U.S. Application Data

(63) Continuation of application No. 16/671,229, filed on Nov. 1, 2019, now Pat. No. 10,912,738, which is a continuation of application No. 15/978,261, filed on May 14, 2018, now Pat. No. 10,517,836, which is a continuation of application No. 15/715,186, filed on Sep. 26, 2017, now Pat. No. 10,449,163, which is a continuation of application No. 13/893,373, filed on May 14, 2013, now Pat. No. 9,801,830, which is a continuation of application No. 13/173,786, filed on Jun. 30, 2011, now abandoned.

(60) Provisional application No. 61/361,159, filed on Jul. 2, 2010, provisional application No. 61/361,129, filed on Jul. 2, 2010, provisional application No. 61/361,126, filed on Jul. 2, 2010, provisional application No. 61/361,154, filed on Jul. 2, 2010, provisional application No. 61/361,146, filed on Jul. 2, 2010, provisional application No. 61/360,982, filed on Jul. 2, 2010, provisional application No. 61/361,135, filed on Jul. 2, 2010.

(51) Int. Cl.
| | |
|---|---|
| *A61K 9/70* | (2006.01) |
| *A61K 9/00* | (2006.01) |
| *A61K 31/192* | (2006.01) |
| *A61K 31/44* | (2006.01) |
| *A61K 47/10* | (2017.01) |
| *A61K 47/36* | (2006.01) |
| *D01D 4/02* | (2006.01) |
| *D01F 1/10* | (2006.01) |
| *D04H 1/728* | (2012.01) |
| *D04H 3/16* | (2006.01) |

(52) U.S. Cl.
CPC .............. *A61K 9/70* (2013.01); *A61K 9/0056* (2013.01); *A61K 9/7007* (2013.01); *A61K 31/192* (2013.01); *A61K 31/44* (2013.01); *A61K 47/10* (2013.01); *A61K 47/36* (2013.01); *D01D 4/025* (2013.01); *D01F 1/10* (2013.01); *D04H 1/728* (2013.01); *D04H 3/16* (2013.01)

(58) Field of Classification Search
None
See application file for complete search history.

(56) References Cited

U.S. PATENT DOCUMENTS

| | | | |
|---|---|---|---|
| 3,723,134 | A | 3/1973 | Chivers |
| 3,849,241 | A | 11/1974 | Butin et al. |
| 4,031,201 | A | 6/1977 | Lostia et al. |
| 4,180,558 | A | 12/1979 | Goldberg et al. |
| 4,349,531 | A | 9/1982 | Mlodozeniec et al. |
| 4,855,326 | A | 8/1989 | Fuisz |
| 5,456,923 | A | 10/1995 | Nakamichi et al. |
| 5,518,730 | A | 5/1996 | Fuisz |
| 5,520,924 | A | 5/1996 | Chapman et al. |
| 5,651,987 | A | 7/1997 | Fuisz |
| 5,705,183 | A | 1/1998 | Phillips et al. |
| 6,497,899 | B2 | 12/2002 | Thombre et al. |
| 7,291,300 | B2 | 11/2007 | Chhabra et al. |
| 7,407,669 | B2 | 8/2008 | Leung et al. |
| 7,491,407 | B2 | 2/2009 | Pourdeyhimi et al. |
| 7,900,713 | B2 | 3/2011 | Chen |
| 9,801,830 | B2 | 10/2017 | Darcy et al. |

(Continued)

FOREIGN PATENT DOCUMENTS

| | | |
|---|---|---|
| DE | 19856668 A1 | 6/2000 |
| EP | 1090928 B1 | 5/2004 |

(Continued)

OTHER PUBLICATIONS

"Medical Dictionary of Bismuth", 2004 published by Hougton Miffin Company, 1 Page.
Borboa, Michele, "10 Tip for Digestive Health", Health and Wellness, posted on May 26, 2008.
International Search Report and Written Opinion; Application Ser. No. PCT/US2011/042641; dated Nov. 25, 2011; 5 pages.
Final Office Action; U.S. Appl. No. 13/173,786 dated Feb. 14, 2013.
Final Office Action; U.S. Appl. No. 13/893,373 dated Mar. 4, 2016.
Final Office Action; U.S. Appl. No. 13/893,373 dated Apr. 22, 2015.
Final Office Action; U.S. Appl. No. 13/893,373 dated Dec. 29, 2016.

(Continued)

*Primary Examiner* — Melissa S Mercier
(74) *Attorney, Agent, or Firm* — Elizabeth A. Conklin

(57) ABSTRACT

A method of delivering a health care active having the steps of administering to a mammal in need of a health benefit or a treatment for a health condition a personal health care article and consuming the article. The article contains one or more filaments that contain a backbone material, a health care active and optionally aesthetic agents, extensional aids, plasticizers, and crosslinking agents.

24 Claims, 3 Drawing Sheets

(56) References Cited

U.S. PATENT DOCUMENTS

| | | | |
|---|---|---|---|
| 10,449,163 B2* | 10/2019 | Darcy | A61K 9/70 |
| 10,517,836 B2* | 12/2019 | Darcy | A61K 31/44 |
| 10,912,738 B2 | 2/2021 | Darcy et al. | |
| 2001/0021517 A1 | 9/2001 | Tripp et al. | |
| 2003/0017208 A1 | 1/2003 | Ignatious et al. | |
| 2004/0086544 A1 | 5/2004 | Bezemer et al. | |
| 2005/0008776 A1 | 1/2005 | Chhabra | |
| 2005/0136112 A1 | 6/2005 | Gonzales et al. | |
| 2006/0083784 A1 | 4/2006 | Ignatious et al. | |
| 2006/0264130 A1 | 11/2006 | Karles et al. | |
| 2008/0220054 A1 | 9/2008 | Shastri et al. | |
| 2009/0022761 A1 | 1/2009 | Zuckermann | |
| 2009/0155326 A1 | 6/2009 | Mack et al. | |
| 2010/0018641 A1 | 1/2010 | Branham et al. | |
| 2010/0021517 A1 | 1/2010 | Ahlers | |
| 2010/0166854 A1 | 7/2010 | Michniak-Kohn et al. | |
| 2010/0170647 A1 | 7/2010 | Edwards et al. | |
| 2010/0196440 A1 | 8/2010 | Stark et al. | |
| 2010/0266668 A1 | 10/2010 | Coffee et al. | |
| 2010/0285101 A1 | 11/2010 | Moore et al. | |
| 2011/0027328 A1 | 2/2011 | Baig | |
| 2011/0129510 A1 | 6/2011 | Liebmann et al. | |
| 2011/0160118 A1 | 6/2011 | Podolsky | |
| 2011/0250256 A1 | 10/2011 | Hyun-Oh et al. | |
| 2012/0172831 A1 | 7/2012 | Darcy et al. | |

FOREIGN PATENT DOCUMENTS

| | | | |
|---|---|---|---|
| JP | 03040879 A2 | 2/1991 | |
| JP | 03101618 A1 | 4/1991 | |
| WO | 199011017 A1 | 10/1990 | |
| WO | 199206603 A1 | 4/1992 | |
| WO | 9602284 A1 | 2/1996 | |
| WO | 2000013680 A2 | 3/2000 | |
| WO | 2001054667 A1 | 8/2001 | |
| WO | 2006106514 A2 | 10/2006 | |
| WO | 2007089259 A1 | 8/2007 | |
| WO | 2009022761 A1 | 2/2009 | |
| WO | WO-2009022761 A1 * | 2/2009 | A61K 47/30 |

OTHER PUBLICATIONS

Final Office Action; U.S. Appl. No. 15/715,186 dated Jul. 15, 2019.
Final Office Action; U.S. Appl. No. 16/671,229 dated Sep. 10, 2019.
Non Final Office Action; U.S. Appl. No. 13/173,786 dated Sep. 24, 2012.
Non Final Office Action; U.S. Appl. No. 13/893,373 dated Aug. 15, 2016.
Non Final Office Action; U.S. Appl. No. 13/893,373 dated Oct. 28, 2015.
Non Final Office Action; U.S. Appl. No. 15/715,186 dated Mar. 19, 2019.
Non Final Office Action; U.S. Appl. No. 16/671,229 dated Jul. 27, 2020.
Non Final Office Action; U.S. Appl. No. 16/671,229 dated Aug. 23, 2019.
Notice of Allowance; U.S. Appl. No. 13/893,373 dated Jun. 26, 2017.
Notice of Allowance; U.S. Appl. No. 15/715,186 dated Aug. 29, 2019.
Notice of Allowance; U.S. Appl. No. 16/671,229 dated Sep. 25, 2019.
Notice of Allowance; U.S. Appl. No. 16/671,229 dated Oct. 15, 2020.

* cited by examiner

METHODS OF DELIVERING AN ORAL CARE ACTIVE BY ADMINISTERING ORAL CARE ARTICLES COMPRISING A FILAMENT

FIELD OF THE INVENTION

The present invention relates to oral care compositions that deliver active agents into the oral cavity in the form of an article that is a dissolvable fibrous web structure.

BACKGROUND OF THE INVENTION

Many personal health care products in the market today are sold containing water. The water in the formula adds to the weight and size of the products and translates into greater shipping and storage costs. Additionally, these types of products also have disadvantages in terms of packaging, storage, transportation, and convenience of use. It can also be difficult to control the dosing of liquid personal health care products. Moreover, the presence of water in personal health care products increases susceptibility to degradation of water unstable ingredients and promotes negative interactions between two or more incompatible materials in an article.

Some personal health care products are swallowable and sold as capsules, pills, caplets, and tablets and users need a drink, such as water, to consume the product. It can be inconvenient for a user to find a drink to consume a personal health care product in this form. Other personal health care products are chewable and sold as tablets. These chewable tablets do not require a drink for consumption. However, they are not durable and tend to break when the user transports them and often have a chalky flavor. Furthermore, pediatric and geriatric patients have difficulty swallowing larger oral dosage forms.

Some personal health care products are available in a dissolvable strip. However, these strips have a low loading capacity which limits the variety and amount of personal health care actives that can be added to the dosage form. Furthermore, these strips and the processes for making the strips do not offer the flexibility and rates of production that personal health care articles comprising one or more filaments offer.

Therefore, a need exists for personal health care articles that do not contain a liquid, can be consumed by the user without a drink, are durable during transport, and can contain broad ranges of health care actives and aesthetic agents, which includes higher levels of health care actives than are currently available in dissolvable strips. The filaments and personal health care articles of this invention can be delivered to the user in need via the oral cavity, mouth, throat, nasal passage, rectum, vagina, skin, eyes, ears and combinations thereof. In one embodiment, the filaments and personal health care articles of this invention interact with the moisture in the oral cavity or mouth to disintegrate and release one or more health care actives that are then consumed by the user.

SUMMARY OF THE INVENTION

An oral care article comprising a nonwoven web comprising a plurality of interwoven filaments, the filaments comprise (a) from about 10% to about 80%, by weight on a dry filament basis of one or more backbone materials, (b) greater than 50% by weight on a dry filament basis, of one or more oral care actives wherein said oral care actives are exposed to conditions of intended use, and (c) less than 10%, by weight of the filament, moisture.

DETAILED DESCRIPTION OF THE INVENTION

Figures 1A, 1B:
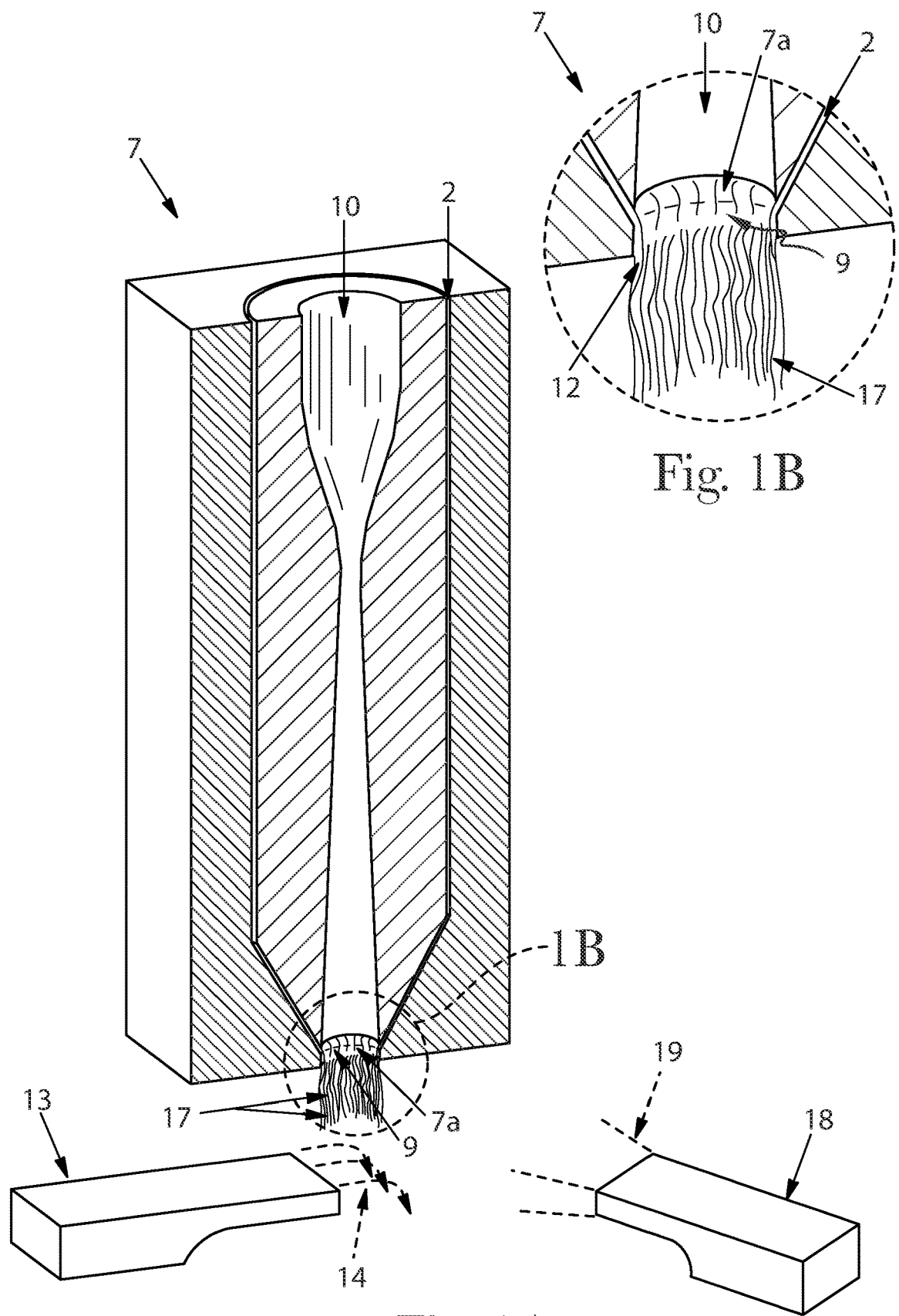
FIG. 1A is a schematic of a circular nozzle for forming filaments according to fluid film fibrillation of the present invention.
FIG. 1B is an enlarged view of a portion of the circular nozzle for forming filaments of FIG. 1A.

An embodiment of the invention can be directed towards a method of delivering a health care active comprising the steps of: (a) administering to a mammal a personal health care article wherein said personal health care article comprises a nonwoven web comprising a filament comprising (i) a backbone material; and (ii) a health care active; and (b) said mammal consumes said article in its intended manner.

These and other limitations of the articles, process, and methods of the present invention, as well as many of the optional ingredients suitable for use herein, are described in detail hereinafter.

As used herein, the term "filament" means a thin, flexible threadlike object that can be used to form a nonwoven web of the present type. The length of a filament can greatly exceed its diameter, i.e. a length to diameter ratio of at least about 10.

The filaments of the present invention may be spun from backbone materials via suitable spinning operations, such as meltblowing or spunbonding.

Filaments are typically considered continuous or substantially continuous in nature.

Filaments are relatively longer than fibers (which are less than 5.08 cm (2 in.) in length). Non-limiting examples of filaments can include meltblown filaments, spunbond filaments, and combinations thereof. In one embodiment, the filaments are meltblown filaments.

In one example, the filaments may be in the form of fibers, such as when the filaments are cut to shorter lengths (such as less than 5.08 cm in length). Thus, in one example, the present invention also includes a fiber comprising the composition of the filament of the present invention.

As used herein, "backbone material" means a composition that is suitable for making a filament such as by meltblowing, spunbonding, or fluid film fibrillation. The backbone material comprises one or more backbone materials that exhibit properties that make them suitable for spinning into a filament.

As used herein, "length", with respect to a filament, means the length along the longest axis of the filament from one terminus to the other terminus. If a filament has a kink, curl or curves in it, then the length is the length along the entire path of the filament.

As used herein, "average diameter", with respect to a filament, is measured according to the Diameter Test Method described herein.

As used herein, the term "disintegratable" and "disintegration" means that the personal health care article, filament, or nonwoven is reduced to components, fragments or particles when exposed to conditions of intended use. In one embodiment, the personal health care article, filament, or nonwoven web partially or completely dissolves. As used herein, the term "dissolves" means that the personal health care article, filament, or nonwoven web is completely solubilized.

As used herein, the term "consumable" as used herein refers to personal health care articles in a form that is deliverable to a mammal in need via the oral cavity including the lips, mouth, tongue, gums, teeth, gingival sulcus, and throat, nasal passages, rectum, vagina, skin (e.g. transdermal drug delivery system or other topical preparations), eyes, ears and combinations thereof.

As used herein "delayed delivery health care actives" refers to a health care active where the health care active is available to the user at a time later than immediately following its administration.

As used herein "extended delivery health care active" refers to a health care active wherein the benefit from the health care active is experienced over time.

As used herein "immediate delivery health care active" refers to a health care active wherein the benefit from the health care active is experienced soon after its administration.

As used herein "targeted delivery health care actives" refers to dosage forms wherein the dosage form is designed to provide the benefit from the health care active to the desired part of the body.

As used herein, the term "applying" includes spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed.

As used herein, "conditions of intended use" means the temperature, physical, chemical, and/or mechanical conditions that a personal health care article comprising one or more filaments of the present invention is exposed to when the personal health care article is used for its designed purpose. The personal health care articles of the present invention can be administered to a mammal via the oral cavity, mouth, throat, nasal passage, rectum, vagina, eye, ear, and combinations thereof. In another embodiment, the personal health care article can be applied to the skin. The conditions of intended use can be the temperature, physical, chemical, and/or mechanical conditions in the oral cavity, mouth, throat, nasal passage, rectum, vagina, eye, ear, or on the skin of a mammal.

"Triggering condition" as used herein means anything, as an act or event that serves as a stimulus and initiates or precipitates a change in the filament, such as a loss or altering of the filament's physical structure and/or a release a health care active.

"Morphology changes" as used herein with respect to a filament's morphology changing means that the filament experiences a change in its physical structure. Non-limiting examples of morphology changes for a filament of the present invention include dissolution, melting, swelling, shrinking, breaking into pieces, lengthening, shortening, peeling, splitting, shredding, imploding, twisting, and combinations thereof. The filaments of the present invention may completely or substantially lose their filament physical structure or they may have their morphology changed or they may retain or substantially retain their filament physical structure as they are exposed to conditions of intended use.

As used herein, "by weight on a dry filament basis" means that the content is determined based on the "bone dry" weight as determined by the Moisture Content Test Method described hereafter.

As used herein and as defined by European Disposables and Nonwovens Association (EDANA), "nonwoven web" means a sheet of continuous filaments of any nature or origin that have been formed into a web by any means, and bonded together by any means, with the exception of weaving or knitting. Felts obtained by wet milling are not nonwovens. In one example, a nonwoven web according to the present invention means an orderly arrangement of filaments within a structure in order to perform a function. In one example, a nonwoven web of the present invention is an arrangement comprising a plurality of two or more and/or three or more filaments that are inter-entangled or otherwise associated with one another to form a nonwoven web.

As used herein, the term "treat" or "treating" includes preventing, alleviating, ameliorating, inhibiting, or mitigating one or more health conditions in a mammal. Non-limiting examples of health conditions can include respiratory conditions, gastrointestinal conditions, central nervous system conditions, pathogenic infections, nutritional deficiencies, and combinations thereof. In one embodiment, the mammal treated may be a human and in another embodiment that mammal can be a companion animal such as a dog, cat or horse.

As used herein, the term "prevent", "preventing" or "prevention" includes averting one or more health care conditions or its associated symptoms from occurring in a mammal, for example when the mammal is predisposed to acquiring the symptoms of coughing, inhibiting the onset of coughing or its associated symptoms; and/or alleviating, reversing, or curing the coughing episode or its associated symptoms.

As used herein, the term "orally administering" and/or "administering" with respect to the mammal means that the mammal consumes or is directed to consume (whether by swallowing or any other means) one or more of the personal health care articles. The mammal may be directed to deliver the personal health care article to the site that is intended to be treated, for example, the oral cavity. The mammal may be directed to consume the personal health care article, and such direction and or delivery may be that which instructs and/or informs the mammal that use of the personal health care article may provide a wellness benefit. The benefit can be instant, delayed or extended. For example, such direction may be oral direction (e.g., through a diagnosis followed by oral instruction from, for example, a physician, pharmacist, veterinarian, or other health professional), radio or television media (e.g., advertisement), or written direction (e.g., through a diagnosis followed by written direction from, for example, a physician, pharmacist, veterinarian, or other health professional (e.g., scripts), sales professional organization (e.g., through, for example, marketing brochures, pamphlets, or other instructive paraphernalia), written media (e.g., internet, electronic mail, or other computer-related media)), and/or packaging associated with the personal health care article (e.g., a label present on a delivery device holding the personal health care article). As used herein, "written" means through words, pictures, symbols, and/or other visible or tactile descriptors. Such information need not utilize the actual words used herein, for example, "respiratory", "symptom", or "mammal", but rather use of words, pictures, symbols, tactile means, and the like conveying the same or similar meaning are contemplated within the scope of this invention.

Health care actives and aesthetic agents useful herein may be categorized or described herein by their health benefit and/or health conditions or their postulated mode of action or function. However, it is to be understood that the health care actives and aesthetic agents useful herein can, in some instances, provide more than one health benefit and/or health conditions or function or operate via more than one mode of action. Therefore, classifications herein are made for the sake of convenience and are not intended to limit an ingredient to the particularly stated function(s) or activities listed.

As used herein, the articles "a" and "an" is understood to mean one or more of the material that is claimed or described, for example, "an aesthetic agent" or "a filament".

All weights, measurements and concentrations herein are measured at 23 degrees Celsius (° C.) and 50% relative humidity on the personal health care article, unless otherwise specified.

All percentages, parts and ratios as used herein are by weight of the total personal health care article, unless otherwise specified. All such weights as they pertain to listed ingredients are based on the active level and, therefore do not include solvents or by-products that may be included in commercially available materials, unless otherwise specified.

The article, process and methods of the present invention can comprise, consist of, or consist essentially of, the essential elements and limitations of the invention described herein, as well as any additional or optional ingredients, components, or limitations described herein or otherwise useful in personal health care articles intended for use or consumption by mammals preferably consumption or use by humans.

Personal Health Care Article

The personal health care article can comprise one or more filaments. The personal health care article can be administered directly to a mammal or incorporated into a device. The use of such a personal health care article allows for easy portability and the ability to better control dosing. Once disintegrated or dissolved, the personal health care article can be consumed by to the user.

The personal health care article can also be delivered via a water insoluble implement or device. For instance, the personal health care article may be attached or glued by some mechanism to an applicator to facilitate application to the oral cavity, mouth, throat, nasal passage, rectum, vagina, skin i.e., a comb, rag, wand, or any other conceivable water-insoluble applicator. In an embodiment, the personal health care article is placed into a liquid, such as water, disintegrated and then administered to the mammal. In another embodiment, the personal health care article is a suppository.

In an embodiment, the personal health care article of the present invention has a basis weight of from about 20 grams per square meter ($g/m^2$) to about 1000 $g/m^2$, in yet another embodiment from about 25 $g/m^2$ to about 500 $g/m^2$, in a further embodiment from about 40 $g/m^2$ to about 250 $g/m^2$, and in another embodiment from about 50 $g/m^2$ to about 100 $g/m^2$.

In an embodiment, the personal health care article of the present invention can be a flat article in the form of a pad, strip, tape, or tablet having a thickness of from about 0.05 millimeter (mm) to about 20 mm, in another embodiment from about 0.05 mm to about 10 mm, in yet another embodiment from about 0.05 mm to about 5 mm, in a further embodiment from about 0.5 mm to about 1 mm, in another embodiment from about 0.05 mm to about 0.5 mm, in yet another embodiment from about 0.05 mm to about 0.25 mm, and in another embodiment from about 0.05 mm to about 0.1 mm, as measured by the Thickness Method described hereafter. In another embodiment, the personal health care article can be formed into a cylindrical shape (e.g. by rolling) having a length from about 0.5 centimeter (cm) to about 10 cm, in another embodiment from about 1 cm to about 5 cm, and in another embodiment from about 1.5 cm to about 3 cm. In another embodiment the personal health care article can be a rectangular prism including a cube wherein the longest sides of the rectangular prism has a length from about 5 mm to 20 mm, in another embodiment from about 10 mm to 15 mm, and in a further embodiment from about 5 mm to about 10 mm, as measured by the Thickness Method described hereafter.

In an embodiment, the personal health care article is in the form of one or more flat sheets or pads of an adequate size to be able to be handled easily by the user. In another embodiment, the flat sheet or pad contains one unit dose of one or more health care actives that can provide one or more health benefits and/or treat one or more health conditions. The personal health care article may have a square, rectangle or disc shape or any other suitable shape. The personal health care article can also be in the form of a continuous strip including delivery on a tape-like roll dispenser with individual portions dispensed via perforations and/or a cutting mechanism.

In one embodiment, the personal health care articles of the present invention can be formed by one or more nonwoven webs. The nonwoven web can be formed by one or more filaments. In another embodiment, the personal health care article may comprise two or more layers wherein at least one of the layers comprises a nonwoven web. In another embodiment, the personal health care article comprises two or more layers wherein each of the layers comprises a nonwoven web. In another embodiment, the personal health care article comprises a first nonwoven web and a second nonwoven web wherein the first nonwoven web comprises a health care active and the second nonwoven web comprises an aesthetic agent.

In an embodiment, the nonwoven web contains more than one filament. In another embodiment, the nonwoven web comprises a first filament and a second filament both comprising a health care active and the health care active can be the same health care active or different health care actives. In another embodiment, the nonwoven web comprises a first filament comprising an immediate delivery health care active and a second filament comprising an extended delivery, a delayed delivery, and/or a targeted delivery health care active. In another embodiment, the nonwoven web comprises a first filament and a second filament wherein the first filament comprises one or more health care actives and the second filament comprises one or more aesthetic agents. In another embodiment, the nonwoven web comprises a first filament, a second filament, and a third filament, wherein each filament comprises a different health care active.

In an embodiment, the nonwoven web or personal health care article comprises a plurality of identical or substantially identical, from a compositional perspective, filaments according to the present invention. In another embodiment, the nonwoven web or personal health care article may comprise two or more different filaments according to the present invention. Non-limiting examples of differences in the filaments may be physical differences such as differences in diameter, length, texture, shape, rigidness, elasticity, and the like; chemical differences such as crosslinking level, solubility, melting point, glass transition temperature (Tg), backbone material, color, amount of health care active, amount of backbone material, presence of a coating composition on the filament, chemical composition of the health care active including whether the health care active is immediate delivery, delayed delivery, extended delivery, or targeted delivery, and the like; differences in whether the filament loses its physical structure when the filament is exposed to conditions of intended use; differences in whether the filament's morphology changes when the filament is exposed to conditions of intended use; and differences in when and where the benefit from the health care active is experienced. In one example, two or more filaments within the personal health care article or nonwoven web may comprise the same backbone material, but have different health care actives.

In an embodiment, the personal health care article or nonwoven web comprises two or more filaments wherein the filaments release the health care actives at different rates. The different rates may be caused by the filaments being positioned at an external surface of the nonwoven web.

In an embodiment, the personal health care article or nonwoven web comprises two or more active agents that are generally considered incompatible with one another in a liquid formulation, for example simethicone and calcium carbonate. Health care actives are incompatible with one another, if when they are in the same composition, at least one of the health care actives has a significant reduction in efficacy, stability, or bioavailability.

In another embodiment, the personal health care article or nonwoven web may exhibit different regions, such as different regions of basis weight, density and/or caliper. In an embodiment, the personal health care article or nonwoven web may comprise discrete regions of filaments that differ from other parts of the nonwoven web.

The personal health care article or the nonwoven web may comprise one or more textured, dimpled or otherwise topographically patterned surfaces including letters, logos or figures. The textured personal health care article can result from the shape of the filament or the nonwoven web, in that the outermost surface of the article contains portions that are raised with respect to other areas of the surface. The raised portions can result from the formed shape of the personal health care article, for example the nonwoven web can be formed in a dimpled or waffle pattern. The raised portions can also be the result of creping processes, imprinted coatings, embossing patterns, or the result of the physical form of the article itself.

In an embodiment, the nonwoven web of the present invention may be pressed into a film to form the personal health care article; this can be done by applying a compressive force and/or heating the nonwoven web to convert the nonwoven web into a film. The film would comprise the health care actives that were present in the filaments of the present invention. The nonwoven web may be completely converted into a film or parts of the nonwoven web may remain in the form of a film after partial conversion of the nonwoven web into the film. In yet another embodiment, the personal health care article may constitute one or more nonwoven webs wherein at least one of the nonwoven webs has been pressed into a film. In another embodiment, the personal health care article comprises two or more nonwoven webs that have been pressed into a film.

In another embodiment, the nonwoven web can be rolled, compressed, cut, or stacked to form a three dimensional personal health care article. For instance, the nonwoven web may be compressed into a pill or tablet, rolled into a cylinder, or compressed or stacked into a rectangular prism to form the personal health care article.

In another embodiment, the personal health care article may constitute one or more layers of nonwoven webs which are optionally bonded together via a bonding means (including heat, moisture, ultrasonic, pressure etc.).

Product Types

Non-limiting examples of product type embodiments for use by the Article and methods of the present invention include personal care articles, oral care articles, personal health care articles, household care articles, and other cleaning articles. Non-limiting examples of oral care articles include teeth cleaning articles, teeth whitening articles, tooth care articles, periodontal gum care articles, denture cleaning articles, tongue cleaning articles, breath freshening articles, fluoride containing articles, mouth rinse articles, anti-cavity articles, and combinations thereof.

In another embodiment, the personal health care article or nonwoven web can be perforated with holes or channels penetrating into or through the personal health care article or nonwoven web. These perforations can be formed as part of making the nonwoven web or personal health care article via spikes extended from the surface of an adjacent belt, drum, roller or other surface. Alternatively, these perforations can be formed after forming the nonwoven web or personal health care article by a process of poking or sticking the porous solids with pins, needles or other sharp objects.

Filament

The personal health care article can comprise one or more filaments. In an embodiment, the filaments of the present invention exhibit a length of greater than about 5.08 cm (2 in.), in an alternate embodiment greater than about 7.62 cm (3 in.), in still another embodiment greater than about 10.16 cm (4 in.), and in another embodiment greater than about 15.24 cm (6 in.).

In one embodiment, the filaments can have an average diameter of less than about 150 micrometers ($\mu$m), in another embodiment less than about 100 $\mu$m, in an another embodiment less than about 10 $\mu$m, and in an yet another embodiment less than about 1 $\mu$m with a relative standard deviation of less than 100%, alternatively less than 80%, alternatively less than 60%, alternatively less than 50%, such as in the range of 10% to 50%, for example. As set forth herein, the significant number means at least 10% of all the filaments, in another embodiment at least 25% of all the filaments, in another embodiment at least 50% of all the filaments, in yet another embodiment at least 75% of all the filaments. In a particular embodiment, the significant number may be at least 99% of all the filaments. In a further embodiment, at least 50% of all the filaments may have an average diameter less than about 10 $\mu$m. The filaments produced by the method of the present disclosure have a significant number of filaments with an average diameter less than about 1 $\mu$m, or sub-micron filaments. In an embodiment, the personal health care article can comprise at least 25% of all the filaments with an average diameter less than about 1 $\mu$m, in another embodiment at least 35% of all the filaments with an average diameter less than about 1 $\mu$m, in another embodiment at least 50% of all the filaments with an average diameter less than about 1 $\mu$m, and in yet another embodiment at least 75% of all the filaments with an average diameter less than about 1 $\mu$m.

In one embodiment, the filament can comprise less than 20% moisture, by weight of the filament, in another embodiment less than about 15% moisture, by weight of the filament, in another embodiment less than about 10% moisture, by weight of the filament, in another embodiment less than about 7%, by weight of the filament, in yet another embodiment less than about 5%, and in another embodiment less than about 3%, by weight of the filament, as measured by the Moisture Content Test Method, described hereafter.

The filament of the present invention can be monocomponent or multicomponent. In one embodiment, the filament is a bicomponent filament. In another embodiment, the filament is a tricomponent filament. The multicomponent filament may be in any form, such as side-by-side, core and sheath, islands-in-the-sea and the like.

In one embodiment, the filaments of the present invention may be meltblown filaments. In another example, the filaments of the present invention may be spunbond filaments. In another example, the filaments may be hollow filaments prior to and/or after release of one or more of its active agents.

In one embodiment, the filament may comprise a health care active within the filament and a health care active on an external surface of the filament, such as a coating on the filament. The health care active on the external surface of the filament may be the same or different from the active agent present in the filament. If different, the health care actives may be compatible or incompatible with one another.

In one embodiment, the filaments may be applied to and/or deposited on a carrier substrate, for example a wipe, paper towel, bath tissue, facial tissue, sanitary napkin, tampon, diaper, adult incontinence article, washcloth, bandage, and the like.

Health Care Active

The filament may comprise one or more health care actives. In an embodiment, one or more health care actives may be uniformly distributed or substantially uniformly distributed throughout the filament. In another embodiment, one or more health care actives may be distributed as discrete regions within the filament. In still another embodiment, at least one health care active is distributed uniformly or substantially uniformly throughout the filament and at least another health care active is distributed as one or more discrete regions within the filament. In still yet another embodiment, at least one health care active is distributed as one or more discrete regions within the filament and at least another health care active is distributed as one or more discrete regions different from the first discrete regions within the filament.

The one or more health care actives can include respiratory agents, gastrointestinal agents, central nervous system (CNS) agents, anti-infective agents, nutritional agents, overall wellbeing agents and combinations thereof. The one or more health care actives of the present invention can also be selected from the group consisting of delayed delivery health care actives, extended delivery health care actives, immediate delivery health care actives, targeted delivery health care actives, and combinations thereof. In an embodiment, one or more health care actives are encapsulated. In one embodiment the health care active is selected from the group consisting of dextromethorphan, fexofenadine, famotidine, naproxen, vitamin $B_9$, and combinations thereof. The personal health care articles of the present invention may also treat one or more health conditions. Non-limiting examples of health conditions can include respiratory conditions, gastrointestinal conditions, CNS conditions, pathogenic infections, nutritional deficiencies, and combinations thereof.

The personal health care articles of the present invention may also provide one or more health benefits. Non-limiting examples of health benefits can include respiratory benefits, gastrointestinal benefits, CNS benefits, anti-infection benefits, nutritional benefits, overall wellbeing benefits, and combinations thereof.

In one embodiment, the health care actives comprise particles. The particles of the health care article are less than about 1 μm, in another embodiment the particles are less than about 750 nanometers (nm), in a different embodiment less than about 500 nm, in yet another embodiment less than about 250 nm, in another embodiment less than about 100 nm, in yet another embodiment less than about 50 nm, in another embodiment less than about 25 nm, in another embodiment less than about 10 nm, in another embodiment less than about 5 nm, and in yet another embodiment less than about 1 nm.

All health care actives may be present from about 10% to about 90%, by weight on a dry filament basis, in another embodiment from about 15% to about 80%, by weight on a dry filament basis, in a different embodiment from about 20% to about 75%, by weight on a dry filament basis, in another embodiment from about 25% to about 70%, by weight on a dry filament basis, in a different embodiment from about 30% to about 60%, by weight on a dry filament basis, and in another embodiment from about 35% to about 60%, by weight on a dry filament basis. In another embodiment, the filament comprises greater than about 10%, by weight on a dry filament basis, health care actives, in yet another embodiment greater than about 15%, by weight on a dry filament basis, health care actives, in another embodiment, greater than about 25%, by weight on a dry filament basis, health care actives, in still another embodiment greater than about 35%, by weight on a dry filament basis, health care actives, in another embodiment greater than about 40%, by weight on a dry filament basis, health care actives, in another embodiment greater than about 45%, by weight on a dry filament basis, health care actives, an in yet another embodiment greater than about 50%, by weight on a dry filament basis, health care actives.

Respiratory Agents

In an embodiment one or more health care actives can be a respiratory agent. Non-limiting examples of respiratory agents can include nasal decongestants, mucolytics, expectorants, antihistamines, antitussives, demulcents, anesthetics, plant-derived respiratory agents, and combinations thereof. Respiratory agents may be used to treat respiratory conditions. Non-limiting examples of respiratory conditions can include influenza, the common cold, pneumonia, bronchitis, and other viral infections; pneumonia, bronchitis, and other bacterial infections; allergies; sinusitis; rhinitis; and combinations thereof. Respiratory agents may provide a respiratory benefit. Non-limiting examples of respiratory benefits can include treating, respiratory symptoms. Non-limiting examples of respiratory symptoms include nasal congestion, chest congestion, rhinorrhea, coughing, sneezing, headache, malaise, sore throat, difficulty breathing, sinus pressure, sinus pain, and combinations thereof.

Non-limiting examples of decongestants can include phenylephrine, 1-desoxyephedrine, ephedrine, propylhexedrine, pseudoephedrine, phenylpropanolamine, and combinations thereof. Decongestants can be present in the filament from about 0.5% to about 40%, by weight on a dry filament basis, alternatively from about 1% to about 30%, by weight on a dry filament basis, and alternatively from about 5% to about 20%, by weight on a dry filament basis.

Non-limiting mucolytics can include ambroxol, bromhexine, N-acetylcysteine, and combinations thereof. Mucolytics can be present in the filament from about 0.5% to about 40%, by weight on a dry filament basis, alternatively from about 1% to about 50%, by weight on a dry filament basis, and alternatively from about 10% to about 60%, by weight on a dry filament basis.

Non-limiting expectorants can include guaifenesin, terpin hydrate, and combinations thereof. Expectorants can be present in the filament from about 1% to about 40%, by weight on a dry filament basis, alternatively from about 2% to about 50%, by weight on a dry filament basis, and alternatively from about 10% to about 60%, by weight on a dry filament basis.

Non-limiting examples of antihistamines can include chlorpheniramine, diphenhydramine, triprolidine, clemastine, pheniramine, brompheniramine, dexbrompheniramine, loratadine, cetirizine and fexofenadine, amlexanox, alkylamine derivatives, cromolyn, acrivastine, ibudilast, bamipine, ketotifen, nedocromil, omalizumab, dimethindene, oxatomide, pemirolast, pyrrobutamine, pentigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine hydrochloride, tripelennamine, chlorcyclizine, clocinizine, homochlorcyclizine, hydroxyzine, tricyclics, phenothiazines, mequitazine, promethazine, thiazinamium methylsulfate, azatadine, cyproheptadine, deptropine, desloratadine, isothipendyl, olopatadine, rupatadine, antazoline, astemizole, azelastine, bepotastine, clemizole, ebastine, emedastine, epinastine, levocabastine, mebhydroline, mizolastine, phenindamine, terfenadine, tritoqualine, and combinations thereof. In one embodiment, the health care active can be fexofenadine. Antihistamines can be present in the filament from about 0.5% to about 30%, by weight on a dry filament basis, alternatively from about 1% to about 20%, by weight on a dry filament basis, alternatively from about 5% to about 15%, by weight on a dry filament basis.

Non-limiting examples of antitussives can include benzonatate, chlophedianol, dextromethorphan, levodropropizine, and combinations thereof. In one embodiment the health care active can be dextromethorphan. Antitussives can be present in the filament from about 0.5% to about 30%, by weight on a dry filament basis, alternatively from about 1% to about 20%, by weight on a dry filament basis, and alternatively from about 5% to about 15%.

Non-limiting examples of demulcents can include glycerin, honey, pectin, gelatin, liquid sugar, and combinations thereof. Demulcents can be present in the filament from about 1% to about 60%, by weight on a dry filament basis, alternatively from about 5% to about 50%, by weight on a dry filament basis, and alternatively from about 10% to about 40%, by weight on a dry filament basis.

Non-limiting examples of anesthetics can include menthol, phenol, benzocaine, lidocaine, hexylresorcinol, and combinations thereof. Anesthetics can be present in the filament from about 0.5% to about 40%, by weight on a dry filament basis, alternatively from about 1% to about 30%, by weight on a dry filament basis, and alternatively from about 5% to about 20%, by weight on a dry filament basis. In certain embodiments, the anesthetics can be present in the filament from about 0.5% to about 20%, and in another embodiment from about 0.5% to about 10%.

Non-limiting examples of plant-derived respiratory agents can include andrographis (*Andrographis paniculata*), garlic (*Allium sativum* L.), *Eleutherococcus senticosus*, a guaiacol component (from oils of *cassia* (*Cinnamomum aromaticum*), clove (*Syzygium aromaticum, Eugenia aromaticum, Eugenia caryophyllata*), or cinnamon (*Cinnamomum zeylanicum, Cinnamomum verum, Cinnamomum loureiroi, Cinnamomum camphora, Cinnamomum tamala, Cinnamomum burmannii*)), borage seed oil (*Borago officinalis*), sage (*Salvia officinalis, Salvia lavandulaefolia, Salvia lavandulifolia*), astragalus (*Astragalus membraneceus*), boneset (*Eupatorium perfoliatum*), chamomile (*Matricaria recutita, Chamaemelum nobile*), cordyceps (*Cordyceps sinensis*), echinacea (*Echinacea angustifolia* DC, *Echinacea pallida, Echinacea purpurea*), elder (*Sambucas nigra* L.), euphorbia, ginseng (*American ginseng, Asian ginseng, Chinese ginseng*, Korean red ginseng, *Panax ginseng: Panax* ssp. Including *P. ginseng* C. C. Meyer, and *P. quinquefolius* L.), goldenseal (*Hydrastis canadensis* L.), greater celandine (*Chelidonium majus*), horseradish (*Armoracia rusticana, Cochlearia armoracia*), maitake mushrooms (*Grifola frondosa*) mistletoe (*Visvum album* L.), geranium (*Pelargonium sidoides*), peppermint/peppermint oil (*Mentha* x *peperita* L.), propolis, slippery elm (*Ulmus rubra* Muhl, *Ulmus fulva* Michx), Sorrel (*Rumex acetosa* L., *Rumex acetosella* L.), thyme/thymus extract (*Thymus vulgaris* L.), wild indigo (*Baptisia australis*), quercetin (a flavanol), and combinations thereof. Plant derived respiratory agents can be present in the filament from about 0.5% to about 50%, by weight on a dry filament basis, alternatively from about 1% to about 40%, by weight on a dry filament basis, and alternatively from about 10% to about 30%, by weight on a dry filament basis.

Gastrointestinal Agents

In an embodiment the one or more health care actives can be a gastrointestinal agent. Non-limiting examples of gastrointestinal agents can include anti-diarrheals, lower gastrointestinal agents, laxatives, anti-emetics, antacids, anti-flattulents, $H_2$ receptor antagonists, proton pump inhibitors, lipase inhibitors, rafting agents, probiotics, prebiotics, dietary fiber, enzymes, plant-derived gastrointestinal agents, anesthetics, and combinations thereof. Gastrointestinal agents may be used to treat gastrointestinal conditions. Non-limiting examples of gastrointestinal conditions can include, gastroesophageal reflux disease, gastritis, peptic ulcers, dyspepsia, irritable bowel syndrome, colitis, Crohn's disease, Barrett's esophagus, gastrinoma, diarrhea, indigestion, constipation, obesity, pouchitis, diverticulitis, enteritis, enterocolitis, dysphagia, inflamed hemorrhoids, food poisoning and other bacterial infections, influenza and other viral infections, and combinations thereof. Gastrointestinal agents may provide gastrointestinal benefits. Non-limiting examples of gastrointestinal benefits can include restoring digestive balance, treating gastrointestinal symptoms, and combinations thereof. Non-limiting examples of gastrointestinal symptoms can include diarrhea, constipation, upset stomach, vomiting, sour stomach, cramps, gas, bloating, stomach ache, lactose intolerances, sore throat, difficulty swallowing, unintentional weight loss, visceral hypersensitivity, feeling of fullness, indigestion, nausea, heartburn, urgency to have a bowel movement, lack of appetite, regurgitation, belching, flatulence, blood in stool, dehydration, and combinations thereof.

Non-limiting examples of anti-diarrheals can include loperamide, pharmaceutically acceptable salts of bismuth, attapulgite, activated charcoal, bentonite, and combinations thereof. The anti-diarrheals can be present in the filament from about 0.25% to about 60%, by weight on a dry filament basis, alternatively from about 0.1% to about 50%, by weight on a dry filament basis, and alternatively from about 5% to about 40%, by weight on a dry filament basis.

Non-limiting examples of lower gastrointestingal agents can include mesalamine, olsalazine sodium, balsalazide disodium, sulfasalazine, tegaserod maleate, and combinations thereof. Lower gastrointestinal agents can be present in the filament from about 0.5% to about 60%, by weight on a dry filament basis, alternatively from about 1% to about 50%, by weight on a dry filament basis, and alternatively from about 5% to about 40%, by weight on a dry filament basis.

Non-limiting examples of laxatives can include bisacodyl, cascara sagrada, castor oil, dietary fiber, resistant starch, resistant maltodextrin, docusate calcium, docusate sodium, lactulose, sennosides, mineral oil, polyethylene glycol 400, polyethylene glycol 3350, and combinations thereof. The laxatives can be present in the filament from about 0.5% to about 85%, by weight on a dry filament basis, alternatively from about 0.1% to about 50%, by weight on a dry filament basis, and alternatively from about 5% to about 40%, by weight on a dry filament basis.

Non-limiting examples of anti-emetics can include cyclizine, meclizine, buclizine, dimenhydrinate, scopolamine, trimethobenzamide, dronabinol, 5-HT$_3$ receptor antagonists, aprepitant, and combinations thereof. Anti-emetics can be present in the filament from about 0.5% to about 50%, by weight on a dry filament basis, alternatively from about 1% to about 40%, by weight on a dry filament basis, and alternatively from about 5% to about 30%, by weight on a dry filament basis.

Non-limiting examples of antacids can include sodium bicarbonate, sodium carbonate, calcium carbonate, magnesium carbonate, magnesium hydroxide, aluminum hydroxide, magaldrate, and combinations thereof. The antacids can be present in the filament from about 10% to about 60%, by weight on a dry filament basis, alternatively from about 25% to about 50%, by weight on a dry filament basis, and alternatively from about 35% to about 45%, by weight on a dry filament basis.

Non-limiting examples of anti-flatulents can include simethicone. The anti-flatulents can be present in the filament from about 0.5% to about 50%, by weight on a dry filament basis, alternatively from about 1% to about 40%, by weight on a dry filament basis, and alternatively from about 5% to about 30%, by weight on a dry filament basis.

Non-limiting examples of H$_2$ receptor antagonists can include famotidine, ranitidine, cimetidine, nizatidine, and combinations thereof. In one embodiment, the health care active can be famotidine. The H$_2$ receptor antagonists can be present in the filament from about 0.5% to about 50%, by weight on a dry filament basis, alternatively from about 1% to about 40%, by weight on a dry filament basis, and alternatively from about 2% to about 30%, by weight on a dry filament basis.

Non-limiting examples of proton pump inhibitors can include omeprazole, lansoprazole, esomeprazole, pantoprazole, rabeprazole, and combinations thereof. The proton pump inhibitors can be present in the filament from about 0.5% to about 40%, by weight on a dry filament basis, alternatively from about 0.5% to about 20%, by weight on a dry filament basis, alternatively from about 0.5% to about 10%, by weight on a dry filament basis, and in yet another embodiment from about 0.5% to about 5%, by weight on a dry filament basis.

Non-limiting examples of lipase inhibitors can include orlistat. The lipase inhibitor can be present in the filament from about 0.5% to about 40%, by weight on a dry filament basis, alternatively from about 1% to about 35%, by weight on a dry filament basis, and alternatively from about 2% to about 30%, by weight on a dry filament basis.

The filament of the present invention may comprise rafting agents. Non-limiting examples of rafting agents can include alginates, fenugreek, guar gum, xanthan gum, carrageenan, and combinations thereof. The rafting agent can be present in the filament from about 1% to about 60%, by weight on a dry filament basis, alternatively from about 5% to about 50%, by weight on a dry filament basis, and alternatively from about 10% to about 40%, by weight on a dry filament basis.

The filament of the present invention may comprise probiotics. Non-limiting examples of probiotics can include microogranisms of the genera *Bacillus, Bacteroides, Bifidobacterium, Enterococcus* (e.g., *Enterococcus faecium*), *Lactobacillus, Leuconostoc, Saccharomyces*, and combinations thereof. In another embodiment of the invention, the probiotic is selected from bacteria of the genera *Bifidobacterium, Lactobacillus*, and combinations thereof.

Non-limiting examples of microorganisms can include strains of *Streptococcus lactis, Streptococcus cremoris, Streptococcus diacetylactis, Streptococcus thermophilus, Lactobacillus bulgaricus, Lactobacillus acidophilus* (e.g., *Lactobacillus acidophilus* strain), *Lactobacillus helveticus, Lactobacillus bifidus, Lactobacillus casei, Lactobacillus lactis, Lactobacillus plantarum, Lactobacillus rhamnosus, Lactobacillus delbruekii, Lactobacillus thermophilus, Lactobacillus fermentii, Lactobacillus salivarius, Lactobacillus reuteri, Bifidobacterium longum, Bifidobacterium infantis, Bifidobacterium bifidum, Bifidobacterium animalis, Bifidobacterium pseudolongum, Saccharomyces boulardii, Pediococcus cerevisiae, Lactobacillus salivarius, Bacillus coagulans*, and combinations thereof. Probiotics can be present in the filament from about 0.025% to about 10%, by weight on a dry filament basis, alternatively from about 0.025% to about 5%, by weight on a dry filament basis, alternatively from about 0.025% to about 3%, by weight on a dry filament basis, and in yet another embodiment from about 0.025% to about 1%, by weight on a dry filament basis.

Non-limiting examples of prebiotics can include carob bean, citrus pectin, rice bran, locust bean, fructooligosaccharide, oligofructose, galactooligosaccharide, citrus pulp, mannanoligosaccharides, arabinogalactan, lactosucrose, glucomannan, polydextrose, apple pomace, tomato pomace, carrot pomace, *cassia* gum, gum karaya, gum talha, gum arabic, and combinations thereof. Prebiotics can be present in the filament from about 1% to about 85%, by weight on a dry filament basis, alternatively from about 10% to about 60%, by weight on a dry filament basis, and alternatively from about 20% to about 50%, by weight on a dry filament basis.

Non-limiting examples of dietary fibers can include, but are not limited to inulin, agar, beta-glucans, chitins, dextrins, lignin, cellulose, modified cellulose, cellulose ethers, hemicelluloses, non-starch polysaccharides, reduced starch, polycarbophil, partially hydrolyzed guar gum, wheat dextrin, and combinations thereof.

In an embodiment, the dietary fiber comprises glucose polymers, preferably those which have branched chains. Among such suitable dietary fibers is one marketed under the tradename "Fibersol2", commercially available from Matsutani Chemical Industry Co., Itami City, Hyogo, Japan.

Other non-limiting examples of suitable dietary fibers can include oligosaccharides, such as inulin and its hydrolysis products commonly known as fructooligosaccharides, galacto-oligosaccharides, xylo-oligosaccharides, oligo derivatives of starch, and combinations thereof.

The dietary fiber can be provided in any suitable form. A non-limiting example is in the form of a plant material which contains the dietary fiber. Non-limiting examples of suitable plant materials can include asparagus, artichoke, onion, wheat, chicory, beet pulp, residues of these plant materials, and combinations thereof.

A non-limiting example of a dietary fiber from such a plant material is inulin extract from extract of chicory. Suitable inulin extracts can be obtained from Orafti SA of Belgium under the trademark Raftiline®. Alternatively the dietary fiber can be in the form of a fructo-oligosaccharide which can be obtained from Orafti SA of Belgium under the trademark Raftilose®. Alternatively, an oliogo-saccharide can be obtained by hydrolyzing inulin, by enzymatic methods, or by using microorganisms as will be understood by those of skill in the art. Alternatively the dietary fiber can be inulin and/or de-sugared inulin available from Cargill Health & Food Technologies, Wayzata, Minn., USA, or from Cosucra SA, Warcoing, Belgium.

In another embodiment, the dietary fiber can be *psyllium*, available, which can be obtained from The Procter & Gamble Company, Cincinnati, Ohio, under the trademark Metamucil®.

The filament of the present invention can comprise enzymes which can include purified enzymes, partially purified enzymes, extracts containing enzymes, and combinations thereof. Enzymes can be produced synthetically, through genetic modification, or they can be produced naturally by plants, animals, or microorganisms. In some embodiments the enzymes are produced by plants such as peppermint, pineapple, or *papaya*. In other embodiments the enzymes are produced by fungi such as *Aspergillus, Candida, Saccharomyces*, and *Rhizopus*. In another embodiment the enzymes are produced by an animal such as a pig or bovine. In certain embodiments, the enzymes help support a more complete digestion of food for gastrointestinal health, regularity, and normal bowel function. In other embodiments, the enzymes can provide wellness benefits or health benefits.

Fiber can be present in the filament from about 1% to about 85%, by weight on a dry filament basis, alternatively from about 10% to about 60%, by weight on a dry filament basis, and alternatively from about 20% to about 50%, by weight on a dry filament basis.

Non-limiting examples of enzymes can include, but are not limited to, proteases, amylases, lipases, and combinations thereof.

Other non-limiting examples of enzymes can include bromelain, pepsin, papain, amyloglucosidase, glucoamylase, malt diastase, maltase, lactase, α-galactosidase, β-glucanase, cellusase, hemilase, hemicellulase, cellulase, xylanase, invertase, pectinase, pancreatin, rennet, phytase, pancrelipase, and combinations thereof. Enzymes can be present in the filament from about 0.5% to about 85%, by weight on a dry filament basis, alternatively from about 5% to about 70%, by weight on a dry filament basis, and alternatively from about 10% to about 50%, by weight on a dry filament basis. In certain embodiments, enzymes can be present in the filament from about 0.5% to about 70%, by weight on a dry filament basis, in another embodiment from about 0.5% to about 50%, by weight on a dry filament basis, in a different embodiment from about 0.5% to about 10%, by weight on a dry filament basis.

Non-limiting examples of plant-derived gastrointestinal agents can include materials from the Ginger family (Zigiberaceae), licorice root (*Glycyrrhizin glabra*), marshmallow root (*Althea officinalis, Althea radix*), fennel oil, fennel seed (*Foeniculum vulgare*), caraway oil, caraway seed (*Carum carvi, Carvi fructus, Carvi aetheroleum*), lemon balm (*Melissae folium, Melissa*), horehound herb (*Murrubii herba*), and flaxseed alpha-linoleic acid (*Lini semen*). Plant derived gastrointestinal agents can be present in the filament from about 0.5% to about 50%, by weight on a dry filament basis, alternatively from about 1% to about 40%, by weight on a dry filament basis, and alternatively from about 10% to about 30%, by weight on a dry filament basis.

Central Nervous System Agents

In an embodiment the one or more health care actives can be a central nervous system (CNS) agent. Non-limiting examples of CNS agents can include sleep aids, nonsteroidal anti-inflammatory drugs, salicylates, opioid analgesics, miscellaneous central nervous system stimulants, anti-emetics, and combinations thereof. Anti-emetics are described herein. CNS agents may be used to treat CNS conditions. Non-limiting examples of CNS conditions can include insomnia, restless leg syndrome, narcolepsy, pain, tobacco dependence, depression, attention deficit disorder, attention deficit hyperactivity disorder, and combinations thereof. Non-limiting examples of pain can include headaches, migraines, arthritis, post-operative pain, dental pain, and combinations thereof. CNS agents may provide CNS benefits. Non-limiting examples of CNS benefits can include increasing alertness, restoring normal circadian rhythm, treating CNS symptoms, and combinations thereof. Non-limiting examples of CNS symptoms can include insomnia, abnormal circadian rhythm, pain, fatigue, drowsiness, difficulty concentrating, irritation, vomiting, nausea, and combinations thereof.

The filament of the present invention can comprise sleep aids. Non-limiting examples of sleep aids can include aolpidem, eszopiclone, zaleplon, doxepin, doxylamine, melatonin, ramelteon, estazolam, flurazepam hydrochloride, quazepam, temazepam, triazolam, and combinations thereof. In certain embodiments, sleep aids can be present in the filament from about 10% to about 60%, by weight on a dry filament basis, in another embodiment from about 10 to about 30%, by weight on a dry filament basis, and in further embodiments from about 10 to about 20%, by weight on a dry filament basis.

Non-limiting examples of nonsteroidal anti-inflammatory drugs (NSAIDs) can include acetaminophen, celecoxib, diclofenac, etodolac, fenoprofen calcium, ibuprofen, ketoprofen, mefenamic acid, meloxicam, naproxen, tolmetin sodium, indomethacin, and combinations thereof. In one embodiment, the health care active can be naproxen. NSAIDs can be present in the filament from about 1% to about 60%, by weight on a dry filament basis, alternatively from about 5% to about 50%, by weight on a dry filament basis, and alternatively from about 10% to about 40%, by weight on a dry filament basis.

Non-limiting examples of salicylates can include aspirin, magnesium salicylate, salsalate, diflunisal, and combinations thereof. Salicylates can be present in the filament from about 1% to about 60%, by weight on a dry filament basis, alternatively from about 5% to about 50%, by weight on a dry filament basis, and alternatively from about 10% to about 40%, by weight on a dry filament basis.

Non-limiting examples of opioid analgesics can include codeine, hydromorphone hydrochloride, methadone hydrochloride, morphine sulfate, oxycodone hydrochloride, and combinations thereof. Opioid analgesics can be present in the filament from about 0.5% to about 40%, by weight on a dry filament basis, alternatively from about 0.5% to about 30%, by weight on a dry filament basis, and alternatively from about 1% to about 20%, by weight on a dry filament basis.

The filament of the present invention can comprise miscelleanous central nervous system stimulants. Non-limiting examples of miscellaneous CNS stimulants can include nicotine, picrotoxin, pentylenetetrazol, and combinations thereof. Miscellaneous central nervous system stimulants can be present in the filament from about 0.1% to about 60%, by weight on a dry filament basis, alternatively from about 1% to about 40%, by weight on a dry filament basis, and alternatively from about 5% to about 30%, by weight on a dry filament basis.

Anti-Infective Agents

In an embodiment the one or more health care actives can be an anti-infective agent. Non-limiting examples of anti-infective agents can include antivirals, antimicrobials, and combinations thereof. Anti-infective agents can be used to treat pathogenic infections. Non-limiting examples of pathogenic infections can include tuberculosis, pneumonia, food poisoning, tetanus, typhoid fever, diphtheria, syphilis, meningitis, sepsis, leprosy, whooping cough, lyme disease, gangrene, urinary tract infections, traveler's diarrhea, methicillin-resistant *Staphylococcus aureus* (MRSA), gonorrhea, scarlet fever, cholera, herpes, hepatitis, human immunodeficiency virus (HIV), influenza, measles, mumps, human papillomavirus, polio virus, giardia, malaria, tapeworm, roundworm, and combinations thereof. Anti-infective agents may provide anti-infective benefits. Non-limiting examples of anti-infective benefits can include treating pathogenic infection symptoms. Non-limiting examples of pathogenic infection symptoms can include fever, inflammation, nausea, vomiting, loss of appetite, abnormal white blood cell count, diarrhea, rash, skin lesions, sore throat, headache, stomach ache, muscle pain, fatigue, cough, chest pain, difficulty breathing, burning during urination, and combinations thereof.

Non-limiting examples of antivirals can include ganciclovir, valganciclovir, acyclovir, famciclovir, valacyclovir, amantadine, ribavirin, rimantidine HCl, oseltamivir phosphate, adefovir dipivoxil, entecavir, and combinations thereof. Antivirals can be present in the filament from about 0.5% to about 60%, by weight on a dry filament basis, alternatively from about 1% to about 30%, by weight on a dry filament basis, and alternatively from about 5% to about 20%, by weight on a dry filament basis. In certain embodiments, the antivirals can be present in the filament from about 20% to about 60%, by weight on a dry filament basis, and alternatively from about 30% to about 60%, by weight on a dry filament basis, and in a further embodiment from about 40% to about 60%, by weight on a dry filament basis.

Non-limiting examples of antimicrobials can include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, rifaximi, nitrofurantoin, and combinations thereof. Antimicrobials can be present in the filament from about 1% to about 50%, by weight on a dry filament basis, alternatively from about 5% to about 40%, by weight on a dry filament basis, and alternatively from about 10% to about 30%, by weight on a dry filament basis.

Nutritional Agents

In an embodiment the one or more health care actives can be a nutritional agent. Non-limiting examples of nutritional agents can include vitamins, minerals and electrolytes, dietary fiber, fatty acids, and combinations thereof. Nutritional agents can be used to treat nutritional deficiencies. Non-limiting examples of nutritional deficiencies can include a depressed immune system, birth defects in newborns, heart disease, cancer, Alzheimer's disease, eye diseases, nightblindness, osteoporosis, beriberi, pellagra, scurvy, rickets, alcoholism, irritable bowel syndrome (IBS), low hormone levels, hypertension, and combinations thereof. Nutritional agents may provide a nutritional benefit. Non-limiting examples of nutritional benefits can include disease prevention, lowering cholesterol, increased energy and alertness, reducing the effects of aging, restoring digestive balance, and treating nutritional deficiency symptoms and combinations thereof. Non-limiting examples of nutritional deficiency symptoms can include fatigue, muscle weakness, irritability, hair loss, unintentional weight loss, unintentional weight gain, decreased mental ability, stress, bone fractures, decreased eyesight, decreased rate of wound healing, hyperactivity, dermatitis, muscle cramping, cardiac arrhythmias, depression, and combinations thereof.

Non-limiting examples of vitamins can include vitamin C, vitamin $D_2$ (cholecalciferol), vitamin $D_3$ (ergocalciferol), vitamin A, vitamin $B_1$ (thiamine), vitamin $B_2$ (riboflavin), vitamin $B_3$ (niacin), $B_5$ (pantothenic acid), vitamin $B_6$ (pyridoxine, pyridoxal, or pyridoxamine), vitamin $B_7$ (biotin), vitamin $B_9$ (folic acid), Vitamin $B_{12}$ (cyanobalmin), vitamin E, and combinations thereof. In one embodiment, the health care active can be vitamin $B_9$. Vitamins can be present in the filament from about 1% to about 85%, by weight on a dry filament basis, alternatively from about 5% to about 60%, by weight on a dry filament basis, and alternatively from about 10% to about 50%, by weight on a dry filament basis.

Non-limiting examples of minerals and electrolytes can include zinc, iron, calcium, iodine, copper, magnesium, potassium, chromium, selenium, and combinations thereof. Minerals and electrolytes can be present in the filament from about 1% to about 85%, by weight on a dry filament basis, alternatively from about 5% to about 60%, by weight on a dry filament basis, and alternatively from about 10% to about 50%, by weight on a dry filament basis.

Non-limiting examples of antioxidants can include, but are not limited to, polyphenols, superfruits, and combinations thereof. Antioxidants can be present in the filament from about 0.5% to about 50%, by weight on a dry filament basis, alternatively from about 1% to about 40%, by weight on a dry filament basis, and alternatively from about 10% to about 30%, by weight on a dry filament basis.

Non-limiting examples of health care actives containing polyphenols can include tea extract, coffee extract, turmeric extract, grapeseed extract, blueberry extract, and combinations thereof. Nonlimiting examples of superfruits can include açaí, blueberry, cranberry, grape, guarana, mangosteen, noni, pomegranate, seabuckthorn, wolfberry (goji), acerola (Barbados cherry, *Malpighia emarginata, Malpighia glabra*), bayberry (yumberry, *Myrica rubra*), bilberry (*Vaccinium myrtillus*), black raspberry (*Rubus occidentalis*), black chokeberry ("aronia", *Aronia melanocarpa*), blackcurrant (*Ribes nigrum*), camu camu (*Myrciaria dubia*), sour (tart) cherry (*Prunus cerasus*), cupuacu (*Theobroma grandiflorum*), durian (*Durio kutejensis*), elderberry (*Sambucus canadensis, Sambucus nigra*), red guava (*Psidium guajava*, many species), Indian gooseberry (amalaka, amla, *Phyllanthus emblica*), kiwifruit (*Actinidia deliciosa*), lingonberry (*Vaccinium vitis-idaea*), lychee (*Litchi chinensis*), muscadine grape (*Vitis rotundifolia*), papaya (*Carica papaya*), pomelo (*Citrus maxima*), saskatoon berry (*Amelanchier*

*alnifolia*, Nutt), tamarind (*Tamarindus indica*), wild cherry (*Prunus avium*) and yuzu (*Citrus ichangensis, C. reticulata*) and combinations thereof.

Non-limiting examples of fatty acids can include Omega-3 fatty acids, Omega-6 fatty acids, and combinations thereof. Fatty acids can be present in the filament from about 1% to about 60%, by weight on a dry filament basis, alternatively from about 5% to about 40%, by weight on a dry filament basis, and alternatively from about 5% to about 20%, by weight on a dry filament basis.

Non-limiting examples of Omega-3 fatty acids can include alpha-linoleic acid, alpha-linolenic acid, stearidonic acid, eicosatrienoic acid, eicosatetraenoic acid, eicosapentaenoic acid, docosapentaenoic acid, docosahexaenoic acid, tetracosapentaenoic acid, tetracosahexaenoic acid, and combinations thereof.

Non-limiting examples of Omega-6 fatty acids can include linoleic acid, gamma-linolenic acid, eicosadienoic acid, dihomo-gamma-linolenic acid, arachidonic acid, docosadienoic acid, adrenic acid, docosapentaenoic acid, and combinations thereof.

Overall Wellbeing Agents

In an embodiment the one or more health care actives can be an overall wellbeing agent. Non-limiting examples of overall wellbeing agents can include energy boosting agents, probiotics, prebiotics, dietary fiber, enzymes, vitamins, minerals and electrolytes, antioxidants, fatty acids, and combinations thereof. Probiotics, prebiotics, dietary fiber, enzymes, vitamins, minerals and electrolyntes, antioxidants, and fatty acids are described herein.

Overall wellbeing agents can be used to provide one or more overall wellbeing benefits. Non-limiting examples of overall wellbeing benefits can include improving and/or maintaining respiratory health, gastrointestinal health, immune health, mobility and joint health, cardiovascular health, skin health, oral/dental health, hair health, eye health, reproductive health including menstrual health, ear, nose and throat health, mental health, energy, normal blood glucose levels, muscle strength, and combinations thereof.

The filament of the present invention can comprise energy boosting agents. Energy boosting actives may provide mammals with more energy or a perception of more energy.

Non-limiting examples of energy boosting agents can include, but are not limited to, caffeine, green and black tea, taurine, *Rhodiola rosea*, Siberian ginseng (*Eleutherococcus senticosus*), CoQ10, L-carnitine, L-Theanine, guarana (*Paullinia cupana*), *Schizandra chinensis*, yerba mate (*Ilex paraguariensis*), goji berry/Wolfberry (*Lycium barbarum* and *L. chinense*), quercetin (a plant-derived flavonol), amalaki/Indian gooseberry (*Phyllanthus emblica*), açaı (from genus *Euterpe*), maca (*Lepidium meyenii*), *Ginkgo biloba*, glucuronolactone, *Panax ginseng* (from species within *Panax*, a genus of 11 species of slow-growing perennial plants with fleshy roots, in the family Araliaceae), *Echinacea* (genus of nine species of herbaceous plants in the Family Asteraceae), rooibos (*Aspalathus linearis*), DHEA, noni (*Morinda* mangosteen (*Garcinia mangostana*), and combinations thereof. Energy boosting agents can be present in the filament from about 0.5% to about 70%, by weight on a dry filament basis, alternatively from about 1% to about 50%, by weight on a dry filament basis, and alternatively from about 10% to about 40%, by weight on a dry filament basis.

Excipients

The personal health care article and filaments can include one or more excipients. Non-limiting examples of excipients can include filament-forming materials, aesthetic agents, and combinations thereof. Non-limiting examples filament-forming materials can include backbone materials, extensional aids, plasticizers, crosslinking agents, and combinations thereof. Non-limiting examples of aesthetic agents can include flavors, colorants, sensates, sweeteners, salivation agents, and combinations thereof.

Backbone Material

The backbone material can comprise any suitable material that exhibits properties suitable for making a filament. Non-limiting examples of backbone materials can include polymers, sugars, sugar alcohols, and combinations thereof. In an embodiment the filament comprises two or more different backbone materials. In another embodiment the filament comprises three or more different backbone materials. In one embodiment, the polymer can function as a backbone material and in certain embodiments can also provide a health benefit The filament can comprise from about 10% to about 80% backbone material, by weight on a dry filament basis, in another embodiment from about 15% to about 75% backbone material, by weight on a dry filament basis, in still another embodiment from about 20% to about 70% backbone material, by weight on a dry filament basis, in another embodiment from about 20% to about 65% backbone material, by weight on a dry filament basis, in still another embodiment from about 25% to about 65%, by weight on a dry filament basis, and in a further embodiment from about 30% to about 60% backbone material, by weight on a dry filament basis.

Polymer

In one embodiment, the backbone material can comprise a polymer. Non-limiting examples of polymers can include naturally sourced polymers, synthetic polymers, and combinations thereof.

Non-limiting examples of naturally sourced polymers can include alginates, gums, protein based polymers, starch based polymers, native starches, modified starches, fiber polymers, other naturally sourced polymers, and combinations thereof.

Non-limiting examples of alginates can include ammonium alginate, calcium alginate, potassium alginate, propylene glycol alginate, and combinations thereof.

Non-limiting examples of gums can include acacia gum, carrageenan, tragacanth gum, guar gum, locust bean gum, xanthan gum, gellan gum, and combinations thereof.

Non-limiting examples of protein based polymers can include whey protein isolate, soy protein isolate, egg albumin, casein, collagen, glutelin, gelatin, gluten, zein, and combinations thereof.

Non-limiting examples of starch based polymers can include cereals, tubers, roots, legumes, fruits, and combinations thereof.

Non-limiting examples of native starches can include can include waxy or high amylase varieties of corn, pea, potato, banana, barley, wheat, rice, sago, amaranth, tapioca, arrowroot, *canna*, sorghum, and combinations thereof.

Non-limiting examples of modified starches can include hydroxypropyl starch, maltodextrin, high amylose starch, and combinations thereof.

Non-limiting examples of fiber polymers can include pectins, fructo-oligosaccharides, inulin, agar, beta-glucans, dextrins, lignin, celluloses, non-starch polysaccharides, reduced starch, polycarbophil, citrus fiber, and combinations thereof.

Non-limiting examples of other naturally sourced polymers can include agar, pullulan, chitin, chitosan, shellac, and combinations thereof.

Non-limiting examples of synthetic polymers can include cellulose derivatives, carbomers, polymethacrylates, other synthetic polymers, and combinations thereof.

Non-limiting examples of cellulose derivatives can include hydroxyethylmethyl cellulose, hydroxylpropylmethyl cellulose, hydroxypropyl cellulose, hydroxypropylethyl cellulose, methylcellulose, hydroxypropyl methylcellulose, and combinations thereof.

Non-limiting examples of carbomers can include carbomer 934, carbomer 934P, carbomer 940, carbomer 94, carbomer 1342, carbomer copolymers, carbomer homopolymers, carbomer interpolymers, and combinations thereof. Some carbomers are available commercially as Carbopol® 934P NF polymer, Carbopol® 971P NF polymer, and Carbopol® 974P NF polymer.

Non-limiting examples of polymethacrylates can include ammonio methacrylate copolymer, basic butylated methacrylate copolymer, methacrylic acid-methyl methacrylate copolymer (1:1), methacrylic acid-ethyl acrylate copolymer (1:1), methacrylic acid-ethyl acrylate copolymer (1:1), methacrylic acid-methyl methacrylate copolymer (1:2), polyacrylate dispersion 30%, methacrylic acid copolymer, amino methacrylate copolymer, ammonio methacrylate copolymer, ammonio methacrylate copolymer dispersion, ethyl acrylate and methyl methacrylate copolymer, and combinations thereof. Some polymethacrylates are available commercially as Eudragit® E 12.5, Eudragit® E 100, Eudragit® E PO, Eudragit® L 12.5 P, Eudragit® L 12.5, Eudragit® L 100, Eudragit® L 100-55, Eudragit® L 30 D-55, Eudragit® S 12.5 P, Eudragit® S 12.5, Eudragit® S 100, Eudragit® FS 30 D, Eudragit® RL 12.5, Eudragit® RL 100, Eudragit® RL PO, Eudragit® RL 30 D, Eudragit® RS 12.5, Eudragit® RS 100, Eudragit® RS PO, Eudragit® RS 30 D, Eudragit® NE 30 D, Eudragit® NE 40 D, Eudragit® NM 30 D, Eastacryl™ 30 D, Kollicoat® MAE 30 DP, Kollicoat® MAE 100 P, Acryl-EZE®, Acryl-EZE® 93 A, and Acryl-EZE® MP.

Non-limiting examples of other synthetic polymers can include polyvinyl alcohol, carboxyvinyl polymers, polyvinyl pyrrolidones, polyethylene oxide, polyoxyethylene, and combinations thereof.

In one embodiment, the polymer of the present invention is selected such that its weight average molecular weight is from about 20,000 Daltons (Da) to about 10,000,000 Da, in an embodiment from about 100,000 Da to about 5,000,000 Da, in yet another embodiment from about 500,000 Da to about 4,000,000 Da, and in still another embodiment from about 1,000,000 Da to about 3,000,000 Da. The weight average molecular weight is computed by summing the weight average molecular weight of each backbone material raw material multiplied by their respective relative weight percentages by weight of the total weight of polymers present within the filament.

In one embodiment, the backbone material is polyvinyl alcohol with a weight average molecular weight from about 10,000 Da to about 250,000 Da, in another embodiment from about 15,000 Da to about 200,000 Da, and in another embodiment from about 20,000 Da to about 150,000 Da.

In one embodiment, the backbone material is selected from the group consisting of alginates, starch based polymers, native starches, modified starches, and combinations thereof with a weight average molecular weight from about 1,000,000 Da to about 6,000,000 Da, in another embodiment from about 1,500,000 Da to about 5,000,000 Da, and in another embodiment from about 2,000,000 Da to about 4,000,000 Da.

In one embodiment, the backbone material is selected from the group consisting of polyvinyl alcohol, pullulan, pectin, corn starch, modified corn starch, hydroxypropyl methylcellulose, and combinations thereof.

Sugar

In one embodiment, the backbone material can be a sugar. Non-limiting examples of sugar can include monosaccharides, disacchairdes, trioses, tetroses, pentoses, hexoses, heptoses, octoses, nonose, sugar alcohols, and combinations thereof.

Non-limiting examples of monosaccharides can include glucose, fructose, and combinations thereof.

Non-limiting examples of disaccharides can include sucrose, maltose, lactose, high fructose corn syrup solids, trehalose, cellobiose, gentiobiose, isomaltose, kojibiose, laminaribiose, mannobiose, melibiose, nigerose, rutinose, xylobiose, lactulose and combinations thereof.

Non-limiting examples of trioses can include glyceraldehydes, dihydroxyacetone, and combinations thereof.

Non-limiting examples of tetroses can include erythrose, threose, erythrulose, and combinations thereof.

Non-limiting examples of pentoses can include arabinose, lyxose, ribose, xylose, ribulose, xylulose, and combinations thereof.

Non-limiting examples of hexoses can include allose, altrose, galactose, glucose, gulose, idose, mannose, talose, fructose, psicose, sorbose, tagatose, and combinations thereof.

Non-limiting examples of heptoses can include mannoheptulose, sedoheptulose, and combinations thereof.

Non-limiting examples of octoses can include octolose, 2-keto-3-deoxy-manno-octonate, and combinations thereof. A non-limiting example of nonose can include sialose.

Non-limiting examples of sugar alcohols can include sorbitol, mannitol, lactitol, isomalt, arabitol, erythritol, glycerol, isomalt, lactitol, maltitol, xylitol, and combinations thereof.

Extensional Aids

In one embodiment, the filament can optionally comprise an extensional aid. Non-limiting examples of extensional aids can include polymers, other extensional aids, and combinations thereof.

In one embodiment, the extensional aids have a weight average molecular weight of at least about 500,000 Da. In another embodiment, the weight average molecular weight of the extensional aid is from about 500,000 to about 25,000,000, in another embodiment from about 800,000 to about 22,000,000, in yet another embodiment from about 1,000,000 to about 20,000,000, and in another embodiment from about 2,000,000 to about 15,000,000. The high molecular weight extensional aids are preferred in some embodiments of the invention due to the ability to increase extensional melt viscosity and reducing melt fracture.

The extensional aid, when used in meltblowing, is added to the composition of the present invention in an amount effective to visibly reduce the melt fracture and capillary breakage of filaments during the spinning process such that substantially continuous filaments having relatively consistent diameter can be melt spun. Regardless of the process employed to produce filaments, the extensional aids, when used, can be present from about 0.001% to about 10%, by weight on a dry filament basis, in one embodiment, and in another embodiment from about 0.005 to about 5%, by weight on a dry filament basis, in yet another embodiment from about 0.01 to about 1%, by weight on a dry filament basis, and in another embodiment from about 0.05% to about 0.5%, by weight on a dry filament basis.

Non-limiting examples of polymers that can optionally be used as extensional aids can include alginates, carrageenans, pectin, chitin, guar gum, xanthum gum, agar, gum arabic, karaya gum, tragacanth gum, locust bean gum, alkylcellulose, hydroxyalkylcellulose, carboxyalkylcellulose, and mixtures thereof.

Nonlimiting examples of other extensional aids can include carboxyl modified polyacrylamide, polyacrylic acid, polymethacrylic acid, polyvinyl alcohol, polyvinylacetate, polyvinylpyrrolidone, polyethylene vinyl acetate, polyethyleneimine, polyamides, polyalkylene oxides including polyethylene oxide, polypropylene oxide, polyethylenepropylene oxide, and mixtures thereof.

Plasticizer

In an embodiment, the filament can optionally comprise a plasticizer. Non-limiting examples of plasticizers can include polyols, polycarboxylic acids, polyesters, other suitable plasticizers, and combinations thereof.

Non-limiting examples of polyols can include glycerin, propylene glycol, polyethylene glycol, sugar alcohols including sorbitol, mannitol, and lactitol; mono di- and oligo-saccharides such as fructose, glucose, sucrose, maltose, lactose, and high fructose corn syrup solids, ascorbic acid, and combinations thereof.

Non-limiting examples of polycarboxylic acids can include citric acid, succinic acid, and combinations thereof.

Non-limiting examples of polyesters can include glycerol triacetate, diethyl phthalate, triethyl citrate, tributyl citrate, acetyl triethyl citrate, acetyl tributyl citrate, and combinations thereof.

Non-limiting examples of other suitable platicizers of the present invention include, but are not limited to, alkyl and allyl phthalates; lactates (e.g., sodium, ammonium and potassium salts); lactic acid; soluble collagen; modified protein; monosodium L-glutamate; proteins and amino acids such as glutamic acid, aspartic acid, and lysine; hydrogen starch hydrolysates; other low molecular weight esters (e.g., esters of C2-C10 alcohols and acids); and any other plasticizer known to one skilled in the art of the food, dietary supplements, and pharmaceutical industries; and combinations thereof.

Crosslinking Agent

In one embodiment the filament can optionally comprise a crosslinking agent that is suitable for crosslinking one or more of the backbone materials. Non-limiting examples of crosslinking agents can include enzymatic crosslinking agents, ionic crosslinking agent, and combinations thereof. Non-limiting examples of ionic crosslinking agents can include calcium carbonate, calcium citrate, calcium citrate malate, calcium chloride, and combinations thereof. In one embodiment, the crosslinking agents can be present from about 0.01% to about 5%, by weight on a dry filament basis, in another embodiment from about 0.1 to about 3%, by weight on a dry filament basis, and in yet another embodiment from about 0.25 to about 2.5%, by weight on a dry filament basis.

Aesthetic Agents

The filaments of the present invention can optionally comprise one or more aesthetic agents. The one or more aesthetic agents can be selected from the group consisting of flavors, colorants, sensates, sweeteners, salivation agents, and combinations thereof. All aesthetic agents can be present from about 0.001% to about 80%, by weight on a dry filament basis, in another embodiment from about 0.005% to about 60%, by weight on a dry filament basis, in still another embodiment from about 0.05% to about 55%, by weight on a dry filament basis, and in another embodiment from about 0.1% to about 50%, by weight on a dry filament basis. All aesthetic agents can be present from about 0.001% to about 60%, by weight of the article, in another embodiment from about 0.005% to about 50%, by weight of the article, in still another embodiment from about 0.05% to about 40%, by weight of the article, and in another embodiment from about 0.1% to about 35%, by weight of the article.

Flavors

The filament can optionally include one or more flavors. Non-limiting examples of flavors that can be used in the present invention can include natural flavoring agents, artificial flavoring agents, artificial extracts, natural extracts and combination thereof. Non-limiting examples of flavors can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, mouth cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, adipic acid, citral, denatonium benzoate, ethyl acetate, ethyl lactate, ethyl maltol, ethylcellulose, fumaric acid, leucine, malic acid, menthol, methionine, monosodium glutamate, sodium acetate, sodium lactate, tartaric acid, thymol, and combinations thereof.

Flavors can be present from about 0.05% to about 50%, by weight of the article, in another embodiment from about 0.01% to about 30%, by weight on a dry filament basis, in still another embodiment from about 0.2% to about 20%, by weight on a dry filament basis, and in another embodiment from about 0.1% to about 15%, by weight on a dry filament basis. Flavors can be present from about 0.05% to about 5%, by weight of the article, in another embodiment from about 0.01% to about 3%, by weight of the article, in still another embodiment from about 0.2% to about 2%, by weight of the article, and in another embodiment from about 0.1% to about 1.5%, by weight of the article.

Colorants

The filament can optionally include one or more colorants. In an embodiment, the colorants provide a visual signal when the filament is exposed to conditions of intended use. Non-limiting examples colorants that may be used in the present invention include FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red

34, D&C red #36, D&C red #39, FD&C red #40, D&C violet #2, FD&C yellow #5, FD&C yellow #6, D&C yellow #7, Ext. D&C yellow #7, D&C yellow #8, D&C yellow #10, D&C yellow #11, and combinations thereof. Colorants can be present from about 0.05% to about 2%, by weight on a dry filament basis or the article, in another embodiment from about 0.01% to about 2%, by weight on a dry filament basis or the article, and in still another embodiment from about 0.02% to about 1.5%, by weight on a dry filament basis or the article.

Sensates

The filaments can optionally include one or more sensates. Non-limiting examples of sensates can include cooling sensates, warming sensates, tingling sensates, and combinations thereof. Sensates are useful to deliver signals to the user.

Non-limiting examples of cooling sensates can include WS-23 (2-Isopropyl-N,2,3-trimethylbutyramide), WS-3 (N-Ethyl-p-menthane-3-carboxamide), WS-30 (1-glyceryl-p-mentane-3-carboxylate), WS-4 (ethyleneglycol-p-methane-3-carboxylate), WS-14 (N-t-butyl-p-menthane-3-carboxamide), WS-12 (N-(4-ethoxyphenyl)-p-menthane-3-carboxamide), WS-5 (Ethyl-3-(p-menthane-3-carboxamido) acetate, Menthone glycerol ketal (sold as Frescolat® MGA by Haarmann & Reimer), (−)-Menthyl lactate (sold as Frescolat® ML by Haarmann & Reimer), (−)-Menthoxypropane-1,2-diol (sold as Coolant Agent 10 by Takasago International), 3-(1-menthoxy)propane-1,2-diol, 3-(1-Menthoxy)-2-methylpropane-1,2-diol, (−)-Isopulegol is sold under the name "Coolact P®" by Takasago International, cis & trans p-Menthane-3,8-diols (PMD38)—Takasago International, Questice® (menthyl pyrrolidone carboxylate), (1R,3R,4S)-3-menthyl-3,6-dioxaheptanoate—Firmenich, (1R,2S,5R)-3-menthyl methoxyacetate—Firmenich, (1R,2S,5R)-3-menthyl 3,6,9-trioxadecanoate—Firmenich, (1R,2S,5R)-menthyl 11-hydroxy-3,6,9-trioxaundecanoate—Firmenich, (1R,2S,5R)-3-menthyl (2-hydroxyethoxy)acetate—Firmenich, Cubebol—Firmenich, Icilin also known as AG-3-5, chemical name 1-[2-hydroxyphenyl]-4-[2-nitrophenyl-]-1,2,3,6-tetrahydropyrimidine-2-one), 4-methyl-3-(1-pyrrolidinyl)-2[5H]-furanone, Frescolat ML—menthyl lactate, Frescolat MGA—menthone glycerin acetal, Peppermint oil, Givaudan 180, L-Monomenthyl succinate, L-monomenthyl glutarate, 3-1-menthoxypropane-1,2-diol—(Coolact 10), 2-1-menthoxyethanol (Cooltact 5), TK10 Coolact (3-1-Menthoxy propane-1,2-diol), Evercool 180 (N-p-benzeneacetonitrile-menthane carboxamide), and combinations thereof. Cooling sensates can be present from about 0.005% to about 60%, by weight on a dry filament basis, in another embodiment from about 0.05% to about 50%, by weight on a dry filament basis, and in still another embodiment from about 0.01% to about 40%, by weight on a dry filament basis. Cooling sensates can be present from about 0.005% to about 10%, by weight of the article, in another embodiment from about 0.05% to about 7%, by weight of the article, and in still another embodiment from about 0.01% to about 5%, by weight of the article.

Non-limiting examples of warming sensates can include TK 1000, TK 1 MM, Heatenol—Sensient Flavors, Optaheat—Symrise Flavors, Cinnamon, Polyethylene glycol, *Capsicum*, Capsaicin, Curry, FSI Flavors, Isobutavan, Ethanol, Glycerin, Nonivamide 60162807, Hotact VEE, Hotact 1MM, piperine, optaheat 295 832, optaheat 204 656, optaheat 200 349, and combinations thereof. Warming sensates can be present from about 0.005% to about 60%, by weight on a dry filament basis, in another embodiment from about 0.05% to about 50%, by weight on a dry filament basis, and in still another embodiment from about 0.01% to about 40%, by weight on a dry filament basis. Warming sensates can be present from about 0.005% to about 10%, by weight of the article, in another embodiment from about 0.05% to about 7%, by weight of the article, and in still another embodiment from about 0.01% to about 5%, by weight of the article.

Non-limiting examples of tingling sensates can include sichuan pepper, hydroxy alpha sanshool, citric acid, Jambu extracts, spilanthol, and combinations thereof. Tingling sensates can be present from about 0.005% to about 10%, by weight on a dry filament basis or the article, in another embodiment from about 0.01% to about 7%, by weight on a dry filament basis or the article, and in still another embodiment from about 0.015% to about 6%, by weight on a dry filament basis or the article.

Sweeteners

The filament can optionally include one or more sweeteners. Sweeteners can be natural or artificial. Non-limiting examples of sweeteners can include nutritive sweeteners, sugar alcohols, synthetic sweeteners, high intensity natural sweeteners, and combinations thereof. All sweeteners can be present from about 0.05% to about 60%, by weight on a dry filament basis or the article, in another embodiment from about 0.1% to about 50%, by weight on a dry filament basis or the article, in yet another embodiment from about 1% to about 10%, by weight on a dry filament basis or the article.

Non-limiting examples of nutritive sweeteners can include sucrose, dextrose, glucose, fructose, lactose, tagatose, maltose, trehalose, and combinations thereof. Nutritive sweeteners can be present from about 0.1% to about 60%, by weight on a dry filament basis or the article, in another embodiment from about 1% to about 50%, by weight on a dry filament basis or the article, and in a further embodiment from about 0.1% to about 10%, by weight on a dry filament basis or the article.

Non-limiting examples of sugar alcohols can include xylitol, sorbiotl, mannitol, maltitol, lactitol, isomalt, erthritol, and combinations thereof. Sugar alcohols can be present from about 0.1% to about 60%, by weight on a dry filament basis or the article, in another embodiment from about 0.11% to about 50%, by weight on a dry filament basis or the article, and in a further embodiment from about 0.1% to about 10%, by weight on a dry filament basis or the article.

Non-limiting examples of synthetic sweeteners can include aspartame, acesulfame potassium, alitame, sodium saccharin, sucralose, neotame, cyclamate, and combinations thereof. Synthetic sweeteners can be present from about 0.05% to about 10% by weight on a dry filament basis or the article, in another embodiment from about 0.1% to about 5%, by weight on a dry filament basis or the article, and in a further embodiment from about 0.25% to about 4%, by weight on a dry filament basis or the article.

Non-limiting examples of high intensity natural sweeteners can include neohesperidin dihydrochalcone, stevioside, rebaudioside A, rebaudioside C, dulcoside, monoammonium glycrrhizinate, thaumatin, and combinations thereof. High intensity natural sweeteners can be present from about 0.05% to about 10% by weight on a dry filament basis or the article, in another embodiment from about 0.1% to about 5%, by weight on a dry filament basis or the article, and in a further embodiment from about 0.25% to about 4%, by weight on a dry filament basis or the article.

Salivation Agents

The filament can optionally include one or more salivation agents. Non-limiting examples of salivation agents include formula (I):

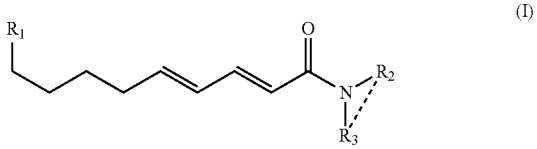

wherein $R_1$ represents C1-C2 n-alkyl; $R_2$ is 2-methyl-1-propyl and $R_3$ is hydrogen, or $R_2$ and $R_3$ taken together is a moiety (designated by the dashed lines) having the formula —(CH$_2$)— wherein n is 4 or 5, and combinations thereof.

In an embodiment, the salivating agent comprises a material wherein $R_2$ is 2-methyl-1-propyl and $R_3$ is hydrogen, in another embodiment the salivating agent comprises a material wherein $R_1$ is C1 n-alkyl, $R_2$ is 2-methyl-1-propyl and $R_3$ is hydrogen. In another embodiment, the salivating agent comprises trans-pellitorin, a chemical having a structure according to formula (II):

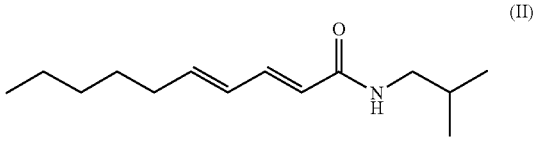 [SMILES: CCCCC/C=C/C=C/C(=O)NCC(C)C]

In another embodiment, the salivation agent could include sodium bicarbonate, sodium chloride, trans pelitorin, and combinations thereof. Salivation agents can be present from about 1% to about 60%, by weight on a dry filament basis, in another embodiment from about 1% to about 50%, by weight on a dry filament basis, and in still another embodiment from about 1% to about 40%, by weight on a dry filament basis. Salivation agents can be present from about 0.005% to about 10%, by weight of the article, in another embodiment from about 0.01% to about 7%, by weight of the article, and in still another embodiment from about 0.015% to about 6%, by weight of the article.

Lathering porous dissolvable solid substrates for the purposes of lathering and/or cleaning comprise from about 10% to about 75%, in one embodiment from about 30% to about 70%, and in another embodiment from about 40% to about 65% by weight of the personal care article of surfactant; wherein the surfactant comprises one or more surfactants from Group I, wherein Group I includes anionic surfactants which are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another embodiment of the present invention the ratio of Group I to Group II surfactants is from about 85:15 to about 40:60. In yet another embodiment of the present invention the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. No. 5,104,646 (Bolich 11'. et al.), U.S. Pat. No. 5,106,609 (Bolich 11'. et al.). The zwitterionic surfactant can be selected from the group consisting of cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coc % leamidopropyl betaine, coco-sultaine, lauramidopropyl betaine, lauryl betaine, lauryl hydroxysultaine, and lauryl sultaine. The amphoteric surfactant can be selected from the group consisting of sodium cocoamphoacetate, sodium cocoamphodiacetate, sodium lauro ampho acetate, sodium lauroamphodiacetate, ammonium lauroamphoacetate, ammonium cocoamphoacetate, triethanolamine lauroamphoacetate, and triethanolamine cocoamphoacetate.

Additional suitable Group I and Group II surfactants include those disclosed in U.S. Patent Application No. 61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790.

Optional Ingredients

The optional ingredients may comprise active agents which may be selected from the group consisting of: personal cleansing and/or conditioning agents such as hair care agents, hair conditioning agents, skin care agents, and skin conditioning agents; laundry care and/or conditioning agents such a fabric care agents, fabric conditioning agents, fabric softening agents, fabric anti-wrinkling agents, fabric care anti-static agents, fabric care stain removal agents, soil release agents, dispersing agents, suds suppressing agents, anti-foam agents, and fabric refreshing agents; hard surface care and/or conditioning agents such as liquid dishwashing agents, powder dishwashing agents, polishing agents, antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, brightening agents, dye transfer-inhibiting agents, water-softening agents, water-hardening agents, pH adjusting agents, acids, bases, medicinal agents, lotions, teeth whitening agents, tooth care agents, mouthwash agents, periodontal gum care agents, sunscreen agents, enzymes, flocculating agents, effervescent agents, preservatives, cosmetic agents, make-up removal agents, lathering agents, deposition aid agents, coacervate-forming agents, clays, thickening agents, latexes, silicas, drying agents, water-treatment agents, odor control agents, antiperspirant agents, cooling agents, warming agents, absorbent gel agents, anti-inflammatory agents, dyes, pigments, edible agents, dietary agents, vitamins, minerals, and combinations thereof.

The optional ingredients may also include those materials approved for use in cosmetics and that are described in reference books such as the CTF A Cosmetic Ingredient Handbook, Second Edition, The Cosmetic, Toiletries, and Perfume Association, Inc. 1988, 1992. Examples of such optional ingredients are disclosed in U.S. Ser. Nos. 12/361, 634, 10/392,422 filed Mar. 18, 2003; and US Publication 2003/0215522A1, dated Nov. 20, 2003.

Release of Health Care Active

One or more health care actives and optional aesthetic agents can be released from the filament when the filament is exposed to a triggering condition. In one example, one or more health care actives may be released from the filament or a part of the filament when the filament or the part of the filament loses its identity, in other words, loses its physical structure. For example, a filament loses its physical structure when the backbone material disintegrates, dissolves, melts or undergoes some other transformative step such that the filament structure is lost. In one example, the one or more health care actives are released from the filament when the filament's morphology changes.

In another example, one or more health care actives may be released from the filament or a part of the filament when the filament or the part of the filament alters its identity, in other words, alters its physical structure rather than loses its physical structure. For example, a filament alters its physical structure when the filament swells, shrinks, lengthens, and/or shortens, but retains its filament structure.

In one example, the filament may release a health care active upon the filament being exposed to a triggering condition that results in the release of the health care active, such as by causing the filament to lose or alter its identity as discussed above. Non-limiting examples of triggering conditions include exposing the filament to solvent, exposing the filament to heat, exposing the filament to cold, exposing the filament to a force, such as a stretching force applied by a user using the filament, exposing the filament to a chemical reaction, exposing the filament to a condition that results in a phase change, exposing the filament to a pH change, exposing the filament to a pressure change, exposing the filament to a temperature change, exposing the filament to light and/or certain wavelengths, exposing the filament to a different ionic strength, exposing the filament to a health care active or aesthetic agent released from another filament, and combinations thereof.

In one embodiment the triggering condition is when the filament is exposed to a temperature from about 68° F. to about 212° F., in another embodiment from about 75° F. to about 140° F., in a further embodiment from about 80° F. to about 110° F., in yet another embodiment from about 93° F. to about 106° F. In another embodiment, the triggering condition is when the filament is exposed to a temperature from about 0° F. to about 60° F., in another embodiment from about 15° F. to about 50° F., and in yet another embodiment from about 25° F. to about 40° F. In another embodiment, the triggering condition is when the filament is exposed to water, saliva, whole blood, blood serum, mucus, perspiration, digestive fluids, tears, or combinations thereof. In another embodiment, the triggering condition is when the filament is exposed to a pH from about 2 to about 8, in another embodiment from about 2 to about 6, in another embodiment from about 2 to about 5, and in yet another embodiment from about 2 to about 3. In one embodiment, the triggering condition is the pH of the duodenum which has a pH from about 5 to about 7.

Coating Composition

The health care active(s) and/or aesthetic agent(s) can optionally be present, at least partially, as a coating composition. The coating composition can be applied to the filament, nonwoven web, or the personal health care article. In certain embodiments, the coating composition covers an outer surface of the filament or the nonwoven web. In another embodiment, the coating composition covers an outer surface of the personal health care article, putting the coating composition in position to immediately contact the target surface (e.g. saliva in the mouth) during use for the release of the health care active(s) and/or aesthetic agent(s).

In an embodiment the coating composition of the present invention may comprise one or more health care actives as defined herein. In another embodiment, the coating composition of the present invention may comprise one or more aesthetic agents as defined herein.

In an embodiment, the filament, nonwoven web, or personal health care article may comprise one or more health care actives which can be the same or different from the health care active present in the coating composition. In another embodiment, the filament, nonwoven web, or personal health care article can comprise a delayed delivery, an extended delivery health care active, and/or a targeted delivery health care active and the coating composition comprises an immediate delivery health care active. In another embodiment, the filament, personal health care article, or nonwoven web can comprise one or more aesthetic agents which can be the same or different from the aesthetic agent in the coating composition.

Process for Manufacture

The filaments, nonwoven web, and/or personal health care article can be prepared by the process comprising: (1) Preparing a processing mixture; (2) Forming filaments; (3) Optionally forming nonwoven webs; (4) Optionally forming a personal health care article; (5) Optionally a second drying step; and (6) Optionally applying a coating composition.

Preparation of Processing Mixture

The filaments of the present invention are made from a processing mixture. The one or more backbone materials and optionally the extensional aid, plasticizer, and crosslinking agents are combined in the presence of water to form the filament-forming mixture. The processing mixture can be mixed by any suitable mixing system such that the filament-forming material(s) are sufficiently combined in the presence of water. In certain embodiments, the backbone material completely dissolves to make a solution. After the filament-forming mixture is made, the health care active(s) and optionally the aesthetic agents, additional extensional aids, plasticizers, and crosslinking agents can be added to form the processing mixture. In one embodiment, the filament-forming mixture is cooled to about room temperature (25° C.) before the health care actives are added and in another embodiment the processing mixture is cooled to about room temperature (25° C.) before the filaments are formed. In one embodiment, the processing mixture is a melt comprising the filament forming materials, health care actives, and optionally the aesthetic agents, extensional aids, plasticizers, and crosslinking agents. The filament forming materials, health care actives, and optionally the aesthetic agents, extensional aids, plasticizers, and crosslinking agents can be dissolved, suspended, or combinations thereof in the processing mixture.

The processing mixture of the present invention has a shear viscosity, as measured according to the Shear Viscosity Test Method described hereafter. In one embodiment, the processing mixture has a shear viscosity of from about 1 pascal·seconds (Pa·s) to about 25 Pa·s, in another embodiment from about 2 Pa·s to about 20 Pa·s, in yet another embodiment from about 3 Pa·s to about 10 Pa·s. This shear viscosity can be achieved by adjusting the amount of water, the amount of the various ingredients dissolved or suspended therein, or both.

The processing mixture may be processed at any convenient temperature: in one embodiment at a temperature of from about 50° C. to about 100° C., in another embodiment, and in another embodiment from about 65° C. to about 95° C., and in another embodiment from about 70° C. to about 90° C.

In one embodiment, the processing mixture comprises both volatile and non-volatile components. The volatile components vaporize during meltblowing and are not present in the filament. Non-limiting examples of volatile components can include water, ethanol, isopropanol, methanol, and combinations thereof. The non-volatile components do not vaporize during meltblowing and are present in the filament. Non-limiting examples of non-volatile ingredients can include health care actives, filament-forming materials, aesthetic agents, and combinations thereof, as described herein. In one embodiment the processing mixture can comprise from about 20% to about 90% non-volatile components, by weight of the processing mixture, in another embodiment from about 30% to about 85% non-volatile components, by weight of the processing mixture, in another embodiment from about 40% to about 75% non-volatile components, by weight of the processing mixture, and in yet another embodiment from about 45% to about 60% non-volatile components, by weight of the processing mixture. In one embodiment the processing mixture can comprise from about 10% to about 80% volatile components, by weight of the processing mixture, in another embodiment from about 15% to about 70% volatile components, by weight of the processing mixture, in another embodiment from about 25% to about 60% volatile components, by weight of the processing mixture, and in yet another embodiment from about 40% to about 55% volatile components, by weight of the processing mixture.

The Capillary Number is a dimensionless number used to characterize the likelihood of droplet breakup. The processing mixture may exhibit a Capillary Number. The processing mixture exhibits a Capillary Number of from about 1 to about 50, in another embodiment from about 3 to about 50, in yet another embodiment from about 5 to about 30, and in another embodiment from about 5 to about 20. A larger Capillary Number indicates greater fluid stability upon exiting the die. In the meltblowing process, the filaments need to have initial stability as they leave the die in order to form a continuous filament.

The Capillary number is defined as follows:

$$Ca = \frac{V * \eta}{\sigma}$$

V is the fluid velocity at the die exit (units of Length per Time)

η is the fluid viscosity at the conditions of the die (units of Mass per Length*Time)

σ is the surface tension of the fluid (units of mass per Time²)

When velocity, viscosity, and surface tension are expressed in a set of consistent units, the resulting Capillary Number will have no units of its own; the individual units will cancel out.

The Capillary number is defined for the conditions at the exit of the die. The fluid velocity is the average velocity of the processing mixture passing through the die opening. The average velocity is defined as follows:

$$V = \frac{Vol'}{Area}$$

Vol'=volumetric flowrate (units of Length³ per Time)
Area=cross-sectional area of the die exit (units of Length²).

When the die opening is a circular hole, then the fluid velocity can be defined as $$v = \frac{Vol'}{\pi * R^2}$$

R is the radius of the circular hole (units of length)

The fluid viscosity will depend on the temperature and may depend of the shear rate. The definition of a shear thinning fluid includes a dependence on the shear rate. The surface tension will depend on the makeup of the fluid and the temperature of the fluid.

Forming Filaments

The filaments can be prepared from a processing mixture. After the processing mixture is prepared, the processing mixture is spun into one or more filaments by any suitable spinning process. In one embodiment, the filaments can be made by meltblowing. In another embodiment, the filaments can be made by fluid film fibrillation.

Electrostatic spinning is a commonly used method of producing sub-micron filaments, but it is not the preferred method herein. In this method, typically, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and filaments are typically produced in small quantities. In an embodiment, the filaments are not derived from electrostatic spinning.

Fluid Film Fibrillation

In one embodiment, the processing mixture is spun into one or more filaments by fluid film fibrillation.

Fluid film fibrillation can comprise a pressurized gas stream flowing within a confined gas passage, comprising upstream converging wall surfaces and downstream diverging wall surfaces into which the processing mixture is introduced to provide an extruded processing mixture film on a heated wall surface that is impinged by the gas stream flowing within the gas passage, effective to fibrillate the processing mixture film into filaments. "Converging" means that the cross-sectional area decreases in the direction of gas flow; and "diverging" means that the cross-sectional area increases in the direction of gas flow.

In one embodiment, the gas passage comprises a first, upstream section into which the gas enters from a supply end, a transition region, and a second, downstream section in which the gas flows to an exit end, wherein the transition region fluidly connects the first section to the second section, and the gas passage ends at the exit end of the second section. In a particular embodiment, the first section of the gas passage has a monotonically decreasing cross-sectional area from the supply end to the transition region, and the second section of the gas passage has a monotonically increasing cross-sectional area from the transition region to the exit end of the second section. At least one flowing processing mixture stream is transmitted through at least one bounded passage which ends in at least one opening in at least one of the opposing heated walls. The processing mixture is in fluid form as it is introduced into the gas passage. Each processing mixture stream extrudes in the form of a film from each opening. Each extruded processing mixture film joins with the gas stream and the processing mixture film is fibrillated to form filaments exiting from the exit end of the second section of the gas passage. For purposes herein, "monotonically decreasing cross-sectional area" means "strictly decreasing cross-sectional area" from the upper inlet) end to the lower end of the upstream nozzle section, and "monotonically increasing cross-sectional area" means "strictly increasing cross-sectional area" from the upper end to the exit end of the downstream section of the nozzle.

In a particular embodiment, each extruded processing mixture film joins with the gas stream in the second section of the gas passage. The introduction of the processing mixture in the second section of the nozzle system on a diverging support wall (that may be heated) can facilitate production of high quality filaments. In a further embodiment, the location where the extruded processing mixture film joins with the gas in the second, downstream section in order to produce the best quality filaments depends on the type of gas, the nozzle geometry, including angles and transitions, and the pressure of the gas, and can be located in the upper half of the second section such as for low gas pressure conditions, and can be located in the lower, downstream half of the second section such as for high gas pressure conditions. In a particular embodiment, only one processing mixture film forms on at least one of the walls that may be heated, the gas pressure exceeds about 10 pounds per square inch (psi), and each processing mixture passage opening from which processing mixture film extrudes is located in a second, downstream half of the second section between the transition region and the exit end of the second section. It has been found that the second half of the downstream second section can provide a gas velocity region where fluid film fibrillation is accomplished very efficiently, yielding high quality filaments.

For the purposes of this disclosure, the bounded passages for pressurized gas and processing mixture together will be referred as "nozzle" or "nozzle system". The nozzle may have bounded passages in a rectangular slot configurations or circular rounded configuration or elongated oval configuration or any configuration that would enable formation of one or more processing mixture film(s) to be impinged by one or more pressurized gas streams. In particular, for a rectangular slot configuration, one or more pressurized gas streams may flow through a bounded rectangular slot passage to impinge on the processing mixture film that forms on a rectangular wall surface to form the processing mixture filaments. In such rectangular slot configuration, the bounded passage for one or more processing mixture may be circular rounded, or elongated oval, or rectangular slot, or any other shape.

Figure 2B:
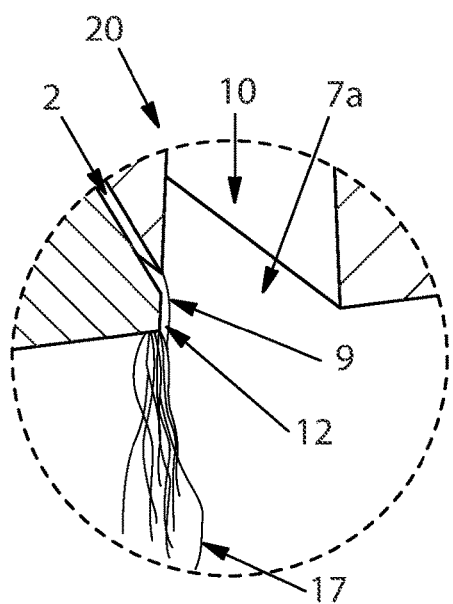
FIG. 2B is an enlarged view of a portion of the slot nozzle for forming filaments of FIG. 2A.
Figure 2A:
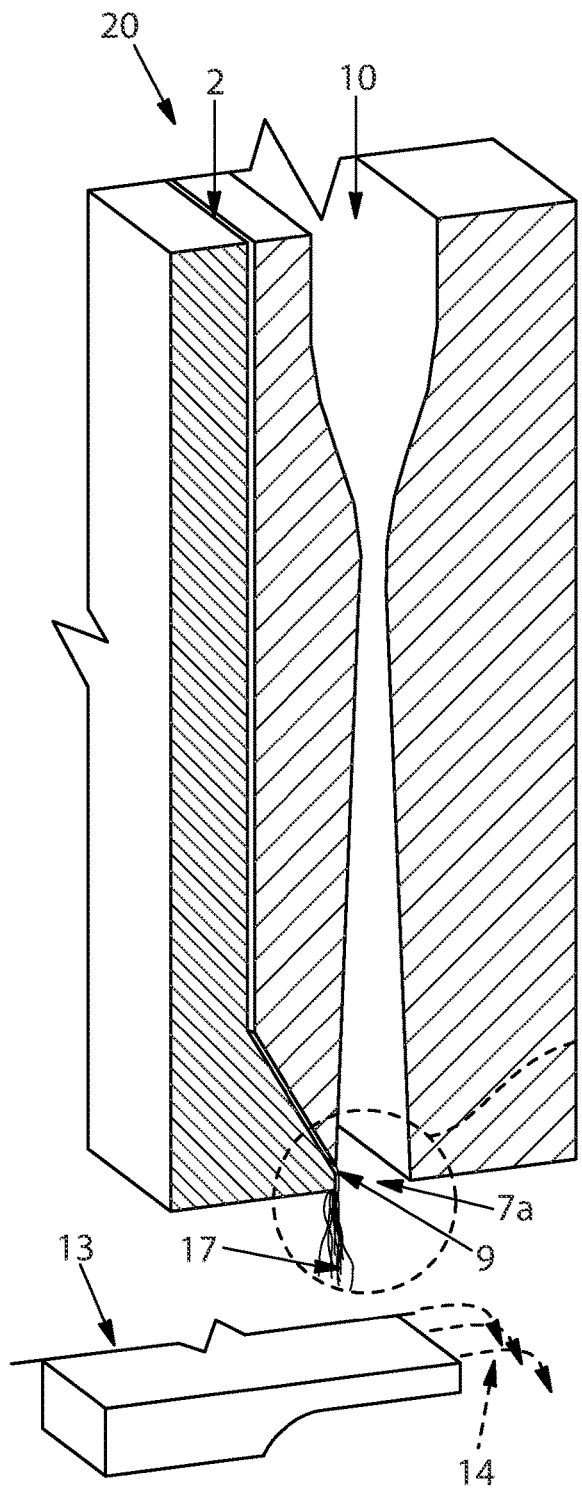
FIG. 2A is a schematic of a slot nozzle for forming filaments according to fluid film fibrillation of the present invention.

An example of a circular nozzle 7 and a slot nozzle 20 for fluid film fibrillation are further illustrated as cross-sectional views in FIGS. 1A and 2A, respectively. These embodiments illustrate a nozzle 7, 20 with orifice 7a, which forms the filaments 17. The process more specifically includes the steps of heating the processing mixture 2 and forming a fluid film 9 across an orifice 7a. The processing mixture will contain the water soluble polymer and any other desired ingredients. The processing mixture 2 is extruded through an orifice 7a, which in turn contains a fiberizing fluid stream 10 such that the processing mixture 2 extrudes as an elongated film 12 (illustrated in Detail A of FIGS. 1 and 2). The orifice 7a may be part of a nozzle 7, 20 and the nozzle 7, 20 may be optimized for process stability. A fiberizing fluid stream 10, such as a pressurized gas stream, is blown to form an elongated film 12. The fiberizing fluid stream 10 will then provide pressure on the inner surface (adjoining fiberizing fluid stream) of the elongated film 12. Thinned wall or weakened portions may form in the elongated film 12 to more easily and controllably enable the formation of filaments including nanofilaments 17. The weakened portions may result from notches or projections located on the outer surface of the jet 10 or on the inner surface of the orifice 7a. The weakened portions may also result spontaneously due to local surface pressure on the fluid film and/or fluid film flow rate differences across the perimeter of the film. The elongated film 12 is then subjected to a fluid to form a multiplicity filaments 17. This fluid can be the pressurized gas stream (the fiberizing fluid stream) 10 or an entraining fluid 14 or any fluid stream. The entraining fluid 14 is from transverse jet 13. If advantageous, a nozzle 18 providing cooling or heating an additional fluid stream 19, that can be used for heating or cooling, to the formed filaments 17 may be used.

The processing mixture 2 is typically heated until it forms a liquid and flows easily. The processing mixture 2 may be at a temperature of from about 0° C. to about 150° C., in one embodiment from about 10° C. to about 120° C., and in another embodiment from about 20° C. to about 100° C. The temperature of the polymer 2 depends on the processing mixture composition. The heated processing mixture 2 is at a pressure from about 15 pounds per square inch absolute (psia) to about 220 psia, in another embodiment from about 20 psia to about 150 psia, and in yet another embodiment from about 25 psia to about 100 psia.

In some cases, the processing mixture film may coalesce immediately after forming. In the case of the coalesced film, in one embodiment, it may be preferred to have thinned walls or weakened portions in the film to aid in the fibrillation. Non-limiting examples of the fiberizing fluid stream are gases such as nitrogen or in another embodiment air or any other fluid compatible (defined as reactive or inert) with processing mixture composition. The fiberizing fluid stream 10 can be at a temperature close to the temperature of the heated processing mixture 2. The fiberizing fluid stream 10 temperature may be at a higher temperature than the heated processing mixture 2 to help in the flow of the processing mixture 2 and the formation of the fluid film 9. Alternatively, the fiberizing fluid stream 10 temperature can be below the heated processing mixture 2 temperature. In one embodiment, the fiberizing fluid stream temperature is about 100° C. above the heated processing mixture 2, in another embodiment about 50° C. above the heated processing mixture 2, or just at temperature of the heated processing mixture 2. The pressure of the fiberizing fluid stream 10 is sufficient to fibrillate the processing mixture into filaments 17 and is above the pressure of the heated processing mixture as it is extruded out of the orifice 7a.

The fiberizing fluid stream 10 may have a velocity of more than about 200 meter per second at the location of film fibrillation. In one embodiment, at the location of film fibrillation, the fiberizing fluid stream velocity will be more than about 300 meter per second, i.e., transonic velocity; in another embodiment more than about 330 meter per second, i.e., sonic velocity; and in yet another embodiment from about 350 to about 800 meters per second (m/s), i.e., supersonic velocity. The fiberizing fluid stream may pulsate or may be a steady flow.

The processing mixture 2 throughput will primarily depend upon the specific processing mixture used, the nozzle design, and the temperature and pressure of the processing mixture. The processing mixture 2 throughput will be more than about 1 gram per minute per orifice, for example in a circular nozzle 7 illustrated in FIG. 1A. In one embodiment, the processing mixture throughput will be more than about 10 gram per minute per orifice and in another embodiment greater than about 20 gram per minute per orifice, and in yet another embodiment greater than about 30 gram per minute per orifice. In an embodiment with the slot nozzle 20, such as the one illustrated in the FIG. 2A, the processing mixture throughput will be more than about 0.5 kilogram per hour per meter width of the slot nozzle. In another slot nozzle embodiment, the processing mixture throughput will be more than about 5 kilogram per hour per meter width of the slot nozzle, and in another slot nozzle embodiment, the processing mixture throughput will be more than about 10 kilogram per hour per meter width of the slot nozzle, and in yet another slot nozzle embodiment, the processing mixture throughput will be more than about 20 kilogram per hour per meter width of the slot nozzle. In certain embodiments of the slot nozzle, the processing mixture throughput may exceed about 40 kilogram per hour per meter width of the slot nozzle. There will likely be several orifices 7a operating at one time which further increases the total production throughput. The throughput, along with pressure, temperature, and velocity, are measured at the orifice 7a for both circular 7 and slot nozzles 20.

The fibrillation of the filaments may occur before the filaments and fluid exit the orifice. Once the elongated film exits the orifice, the filaments are formed. Commonly, the formation of filaments occurs immediately upon exiting the orifice. One or more fluid streams may be used to form the multiplicity of filaments. The fiberizing fluid stream 10 can be the fluid stream adjoining the processing mixture film, an entraining fluid, or any other fluid stream. Optionally, an entraining fluid 14 can be used to induce a pulsating or fluctuating pressure field to help in forming a multiplicity of filaments 17. Non-limiting examples of the entraining fluid 14 are pressurized gas stream such as compressed air, nitrogen, oxygen, or any other fluid compatible (defined as reactive or inert) with the processing mixture composition. As shown in FIGS. 1 and 2, the entraining fluid 14 may be provided by a transverse jet 13 which is located to direct the flow of entraining fluid 14 over and around the elongated film 12 and filament 17 forming region. The entraining fluid 14 can have a low velocity or a high velocity. The entertaining fluid with a high velocity can have a velocity near sonic speed (i.e. about 343.2 m/s) or supersonic speeds (i.e. greater than about 343.2 m/s). An entraining fluid with a low velocity will typically have a velocity of from about 1 to about 100 m/s and in another embodiment from about 3 to about 50 m/s. It is desirable to have low turbulence in the entraining fluid stream 14 to minimize filament-to-filament entanglements, which usually occur due to high turbulence present in the fluid stream. The temperature of the entraining fluid 14 can be the same as the above fiberizing fluid stream 10, or a higher temperature to aid drying of filaments, and ranges from about 80° C. to 300° C. and in another embodiment from about 100° C. to about 250° C. The moisture content or the relative humidity of the entraining fluid 14 when used as drying fluid is very low, generally less than 20%, in another embodiment less than 10%, in another embodiment less than 5%, and in yet another embodiment less than 1%.

Optionally, an additional fluid stream 19, that can be used for heating or drying, can also be used. The additional fluid stream 19 may be a pressurized gas stream such as compressed air, nitrogen, oxygen, or any other fluid compatible (defined as reactive or inert) with the processing mixture composition. This additional fluid stream 19 is located to direct fluid into the filaments 17 to dry the filaments. It is desirable to have low turbulence in the additional fluid stream 19 to minimize filament-to-filament entanglements, which usually occur due to high turbulence present in the fluid stream. If the additional fluid is used as a heating or drying fluid, it is at a temperature of from about 80° C. to 300° C. and typically from about 100° C. to about 250° C. The moisture content or the relative humidity of the additional fluid stream when used as drying fluid is very low, generally less than 20%, in one embodiment less than 10%, in yet another embodimentless than 5%, and in yet another embodiment less than 1%. The additional fluid stream 19 may form a "curtain" or "shroud" around the filaments exiting from the nozzle. Any fluid stream may contribute to the fiberization of the processing mixture and can thus generally be called fiberizing fluid streams.

The filaments may be partially or completely dried in flight to the collector by any or combination of the fiberizing fluid streams—the fiberizing fluid stream 10, the entraining fluid 14, or the additional fluid stream 19. Alternatively, the fiberizing fluid stream 10 or the first pressurized gas stream may be the only fluid stream used for fibrillation and partially or completely drying the processing mixture filaments. In such instance, the drying fluid stream is continuation of the fiberizing fluid stream 10. Alternatively, the fiberizing fluid stream 10 and the second entraining fluid stream 14 may the fluid streams used for fiberizing and drying, respectively. Alternatively, the fiberizing fluid stream 10 and the additional fluid stream 19 may be used for fiberizing and drying, respectively. In a particular embodiment, the additional fluid stream 19 may be adjacent to the fiberizing fluid stream 10. In another embodiment the additional fluid stream 19 may be at an angle to the fiberizing fluid stream 10 after exiting the nozzle. The angle of the additional fluid stream 19 may range from about 0° (parallel) to 90° (perpendicular) to the fiberizing fluid stream 10 as it exits the nozzle. The additional fluid stream 19 can have a low velocity or a high velocity. The additional fluid stream with a low velocity can have a velocity of from about 1 m/s to about 100 m/s and in one embodiment from about 3 m/s to about 50 m/s. The additional fluid stream with a high velocity can have a velocity of greater than about 300 m/s, in another embodiment greater than about 330 m/s, and in yet another embodiment from about 350 m/s to about 700 m/s. One or more drying fluid stream(s) either completely or partially dry the in-flight filaments fibrillated from the processing mixture film. In a particular embodiment, one or more drying fluid stream(s) can partially dry the filaments or dry the filaments to the desired final moisture content. In one embodiment, the filaments are dried to a final moisture content of less than about 20%, in another embodiment less than about 15%, in another embodiment less than about 10%, in another embodiment less than about 7%, in yet another embodiment less than about 5%, in another embodiment less than about 3%.

Meltblowing

In one embodiment, the processing mixture is spun into one or more filaments by meltblowing. For example, the processing mixture may be pumped from an extruder to a meltblown spinnerette. Upon exiting one or more of the filament-forming holes in the spinnerette, the processing mixture is attenuated with air to create one or more filaments.

Figure 3:
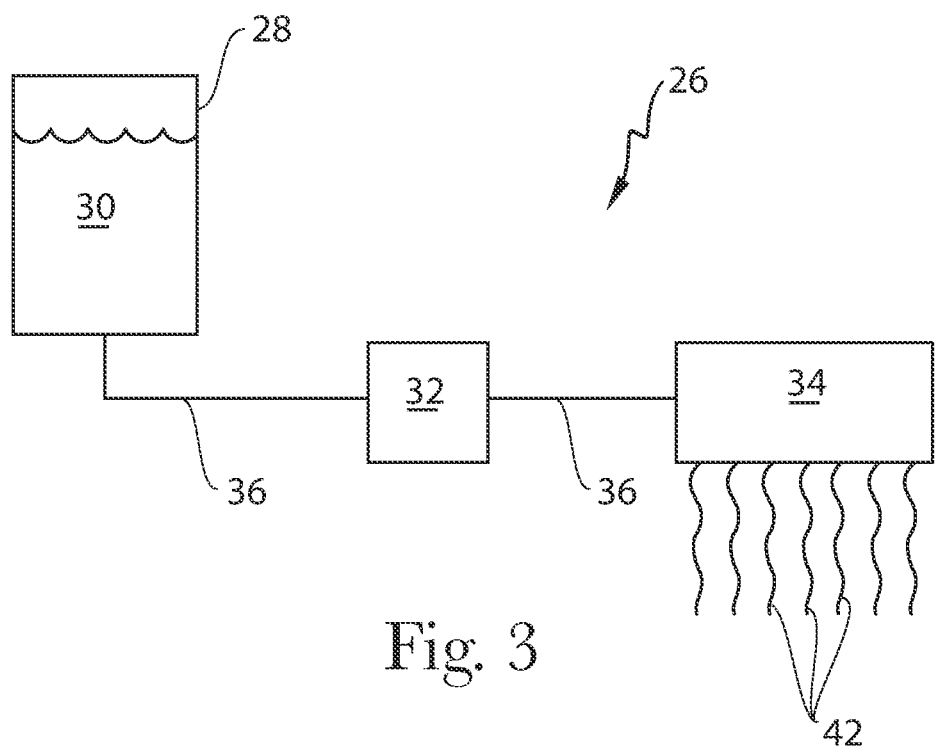
FIG. 3 is a schematic representation of an apparatus suitable for making a filament according to meltblowing of the present invention.
Figure 4:
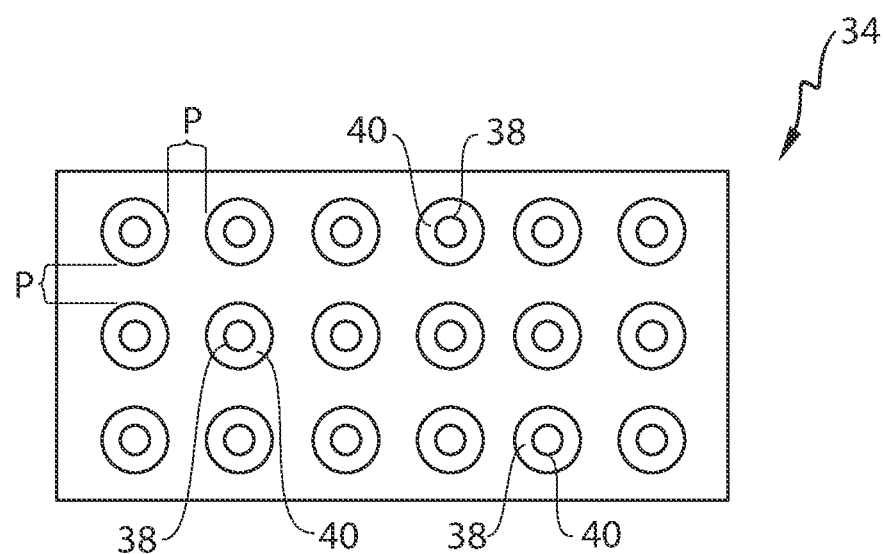
FIG. 4 is a schematic representation of a die suitable for forming a filament according to the meltblowing of the present invention.

In one embodiment, the filaments according to the present invention are produced by using a small-scale apparatus 26, a schematic representation of which is shown in FIGS. 3 and 4. In this nonlimiting embodiment, demonstrated in FIG. 1, the processing mixture is in tank 30 and then goes through pipe 36 to a pump 32 (for example a Zenith®, type PEP II pump having a capacity of 5.0 cubic centimeters per revolution (cc/rev), manufactured by Parker Hannifin Corporation, Zenith Pumps division, of Sanford, N.C., USA). The pump then pumps the processing mixture through a pipe 36 to a die 34. The processing mixture material flows to a die is controlled by adjusting the number of revolutions per minute (rpm) of the pump. The die 34 as shown in FIG. 4 has two or more rows of circular extrusion nozzles 38 spaced from one another at a pitch P of about 1.524 millimeters (about 0.060 inches). The nozzles 38 have individual inner diameters of about 0.305 millimeters (about 0.012 inches) and individual outside diameters of about 0.813 millimeters (about 0.032 inches). Each individual nozzle 38 is encircled by an annular and divergently flared orifice 40 to supply attenuation air to each individual nozzle 38. The processing mixture 30 that is extruded through the nozzles 38 is surrounded and attenuated by generally cylindrical, humidified air streams supplied through the orifices 40 encircling the nozzles 38 to produce the filaments 42. Attenuation air is provided by heating compressed air from a source by an electrical-resistance heater, for example, a heater manufactured by Chromalox, Division of Emerson Electric, of Pittsburgh, Pa., USA. An appropriate quantity of steam is added to the attenuation air to saturate or nearly saturate the heated air at the conditions in the electrically heated, thermostatically controlled delivery pipe. Condensate is removed in an electrically heated, thermostatically controlled, separator.

The filaments may then be partially dried or dried to the desired final moisture content to remove any remaining volatile components used for processing. In one embodiment, the filaments are dried immediately after they are extruded. The filaments can be dried by a drying air stream having a temperature of from about 149° C. (about 300° F.) to about 315° C. (about 600° F.), in another embodiment from about 163° C. (about 325° F.) to about 260° C. (about 500° F.), and in a further embodiment from about 177° C. (about 350° F.) to about 232° C. (about 450° F.). In one embodiment the filaments are dried by the air stream for less than about 30 seconds, in another embodiment for less than about 15 seconds, in another embodiment less than about 5 seconds, in yet another embodiment less than about 1 second, and in another embodiment less than about 0.5 seconds. In one embodiment, the air stream can be heated by an electrical resistance heater supplied through drying nozzles discharged at an angle of about 90° relative to the general orientation of the filaments being extruded.

The filaments can be partially dry or dried to the desired final moisture content. In one embodiment, the filaments are dried to a final moisture content of less than about 20%, in another embodiment less than about 15%, in another embodiment less than about 10%, in another embodiment less than about 7%, in yet another embodiment less than about 5%, in another embodiment less than about 3%.

Forming and Processing a Nonwoven Web

The process of the present invention may optionally comprise a step of collecting a plurality of the filaments to form a nonwoven web.

In one embodiment, the partially dry or dried to desired moisture content filaments are laid down on a collector to form a web. The collector is typically a conveyor belt or a drum. The collector can be porous and vacuum may be applied to provide suction to aid filament lay down on the collector. The distance from the orifice to the collector distance, commonly called die-to-collector distance (DCD), can be optimized for desired nonwoven web properties. It may be desired to utilize more than one DCD used in a nonwoven web, to change the DCD during production, or to have different beams with different DCDs. It may be desirable to form a nonwoven web with different uniformities by changing the DCD. If the DCD is such that filaments are not sufficiently dried before depositing on the collector, the wet or insufficiently dry filaments may coalesce to form blobs or bundles that may not be desirable and would constitute as defects. Alternatively, it may be desirable for a personal health care article to have some or all filaments coalesce completely or partially, e.g., to have structural integrity. If the DCD is large and such that filaments are sufficiently dried, the filaments may entangle or stick to one another, but not coalesce, to form bundles or ropes that may not be desirable. Therefore, depending on the desired personal health care article, the DCD may be set to form nonwoven web with desirable uniformity and sufficient dryness. Alternatively, the nonwoven webs of desirable uniformity may be further dried to obtain moisture content desired in the Article.

Additionally, the die-to-collector distance may be altered along with the vacuum underneath the collector to obtain desired density of the web. Generally, the shorter DCD and/or higher vacuum provides denser nonwoven webs relative to the larger DCD. At shorter DCD and/or higher vacuum, the filaments tend to be "forced" together tightly by the fiberizing fluid jet and/or vacuum suction, while at the larger DCD and/or lower vacuum, the filaments stay fluffy and thus lower density. Therefore, depending on the desired Article density, it may be desirable to optimize DCD and/or vacuum for uniformity, dryness, and density.

The nonwoven webs of the processing mixture may be formed a desired shape or shapes including, but not limited to (i) depositing the nonwoven web to specially designed molds comprising a non-interacting and non-stick surface including Teflon, metal, HDPE, polycarbonate, neoprene, rubber, LDPE, glass and the like; (ii) depositing the nonwoven web into cavities imprinted in dry granular starch contained in a shallow tray, otherwise known as starch moulding forming technique; and (iii) depositing the nonwoven web onto a continuous belt or screen comprising any non-interacting or non-stick material Teflon, metal, HDPE, polycarbonate, neoprene, rubber, LDPE, glass and the like which may be later stamped, cut, embossed or stored on a roll.

Optionally Forming a Personal Health Care Article

In an embodiment, the nonwoven web of the present invention may then be post-processed by subjecting the filament or nonwoven web to a post-processing operation. Nonlimiting examples of post-processing operations include curing, embossing, thermal bonding, humidifying, perfing, calendering, printing, differential densifying, tuft deformation generation, and other known post-processing operations.

The nonwoven webs and/or filaments may be formed into a desired shape or shapes to form a personal health care article. This includes, but is not limited to (i) depositing the nonwoven web and/or filaments into specially designed molds comprising a non-interacting and non-stick surface including Teflon™, metal, HDPE, polycarbonate, neoprene, rubber, LDPE, glass and the like; (ii) depositing the nonwoven web and/or filaments into cavities imprinted in dry granular starch contained in a shallow tray, otherwise known as starch molding forming technique; and (iii) depositing the nonwoven web and/or filaments onto a continuous belt or screen comprising any non-interacting or non-stick material Teflon™, metal, HDPE, polycarbonate, neoprene, rubber, LDPE, glass and the like which may be later stamped, cut, embossed or stored on a roll.

In an embodiment, the personal health care article of the present invention can be a flat article in the form of a pad, strip, tape, tablet, cylinder, sphere, or rectangular prism.

Optionally Drying the Nonwoven Web and/or the Filaments

The nonwoven webs and/or filaments can be dried if they are not at the desired final moisture level. This drying process may be accomplished by any suitable means including, but not limited to (a) multi-stage inline dryers using convection or through-air drying; (b) drying room(s) including rooms with controlled temperature and pressure or atmospheric conditions; (c) ovens including non-convection or convection ovens with controlled temperature and optionally humidity; (d) truck/tray dryers, impingement ovens; (e) rotary ovens/dryers; (f) inline roasters; (g) rapid high heat transfer ovens and dryers; (h) dual plenum roasters, and (i) conveyor dryers.

Optionally Applying a Coating Composition

A coating composition may be imparted during any of the above described processing steps. The coating composition can be applied to the filament, nonwoven web, and/or the personal health care article. The coating composition can be applied by any suitable mechanical, chemical, or other means to produce a coating composition comprising the health care actives or aesthetic agents.

The coating composition can be applied by spraying, dusting, sprinkling, coating, surface-printing (e.g., in the shape of a desired adornment, decoration, or pattern), pouring on, injecting into the interior, dipping, or by any other suitable means, such as by use of a depositor, sifter, or powder bed. The coating composition can be applied over portions or entire regions of the filament, nonwoven, or personal health care article, and can be applied in a manner to adorn, decorate, form a logo, design, etc.

When the coating compositions are applied to the filaments, nonwoven webs, or personal health care articles as a fluid the fluid can be applied as a spray, a gel, or a cream coating.

When the coating compositions are a powder, the powder can be applied by allowing the filaments, nonwoven webs, or personal health care article to have a tacky surface by drying the filament or nonwoven web to a specific moisture content before applying the powder to facilitate the adherence of the coating composition. In another embodiment, a surface of the filament, nonwoven web, or personal health care article is brushed with a cotton swab dipped in distilled water and then the powder can be applied. In another embodiment, the filament or nonwoven web is placed in a bag, tray, belt, or drum containing or otherwise exposed to the powder and agitated, rolled, brushed, vibrated or shaken to apply and distribute the powder, either in a batch or continuous production manner Other powder application methods may include powder sifters, electrostatic coating, tribo charging, fluidized beds, powder coating guns, corona guns, tumblers, electrostatic fluidized beds, electrostatic magnetic brushes, and/or powder spray booths.

When the coating composition comprises two or more health care actives and/or aesthetic agents the two or more health care actives and/or aesthetic agents can be blended or otherwise combined together within a single coating composition or they may be applied via a multiplicity of different coating compositions that may or may not be in contact with one another (applied as layers or to differing regions of the filament, nonwoven web, or personal health care article and combinations thereof). The two or more health care actives and/or aesthetic agents can also be applied to different regions of the filament, nonwoven web, or personal health care article. For instance, in one embodiment the personal health care article is a pad and a first coating composition is applied to one side and a second coating composition is applied to the second pad and the first coating composition and the second coating composition are different.

In certain embodiments, the personal health care article contains a coating composition that can be situated below the surface of the personal health care article. For instance, the personal health care article could contain dimples and the coating composition could be located within the dimples of the personal health care article. In another embodiment, the coating composition may permeate the personal health care article in whole or in part to form the personal health care article.

In another embodiment, the personal health care article comprises a first nonwoven web and a second nonwoven web, and the coating composition is situated between the first nonwoven web and the second nonwoven web. In this nonlimiting embodiment, the two nonwoven webs can be joined together (e.g., via sealing the adjoining surfaces or edges with a thin layer of water and/or plasticizer so as to not substantially dissolve the nonwoven web and applied pressure to induce adhesion). Alternatively, in certain embodiments, the coating composition may be on one nonwoven web which is folded over to form a pouch, encasing the coating composition.

Test Methods

Diameter Test Method

The diameter of the filaments and the diameter of the filaments in a sample of a nonwoven web or personal health care article is determined by using a Scanning Electron Microscope (SEM) or an Optical Microscope and an image analysis software. A magnification of 200 to 10,000 times is chosen such that the filaments are suitably enlarged for measurement. When using the SEM, the samples are sputtered with gold or a palladium compound to avoid electric charging and vibrations of the filaments in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in µm. Several filaments are thus randomly selected across the sample of the web using the SEM or the optical microscope. At least two specimens from the web (or web inside a product) are cut and tested in this manner Altogether at least 100 such measurements are made and then all data are recorded for statistic analysis. The recorded data are used to calculate average (mean) of the filament diameters, standard deviation of the filament diameters, and median of the filament diameters.

Another useful statistic is the calculation of the amount of the population of filaments that are below a certain upper limit. Suitable non-limiting upper limits for the present invention are about 1 µm, in another embodiment about 3 µm, in another embodiment about 5 µm, in another embodiment about 10 µm, and in another embodiment about 100 µm. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. The measured diameter (in microns) of an individual circular filament is denoted as $d_i$.

In case the filaments have non-circular cross-sections, the measurement of the filament diameter is determined as and set equal to the hydraulic diameter which is four times the cross-sectional area of the filament divided by the perimeter of the cross of the filament (outer perimeter in case of hollow filaments). The number-average diameter, alternatively average diameter is calculated as:

$$d_{num} = \frac{\sum_{i=1}^{n} d_i}{n}$$

Moisture Content Test Method

The moisture content present in the filament of the present invention is measured using the following Moisture Content Test Method.

A filament or nonwoven web or portion thereof (hereinafter "sample") is placed in a conditioned room at a temperature of 23° C. and a relative humidity of 50% until the weight of the sample reaches equilibrium (i.e., no further weight change is detected within a 5 minute period). Record this weight as the "equilibrium weight." Next, place the sample in an oven at 70° C. for 24 hours to dry the sample. After the 24 hours, immediately weigh the sample and record the weight of the sample at its "bone dry" weight.

The water content of the sample is calculated as follows:

% Moisture in Sample=(Equilibrium weight−Bone dry weight)/Bone dry weight

Thickness Method

The thickness of the personal health care article is taken as the maximum distance in the shortest direction and is measured in millimetres (mm). The thickness is calculated as the length obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams (g), which measures thickness at an application pressure of about 0.009 psi (6.32 g/cm²).

The thickness of the personal health care article is measured by raising the platen, placing a section of the sample on the stand beneath the platen, carefully lowering the platen to contact the sample, releasing the platen, and measuring the thickness of the sample in millimeters on the digital readout. The sample should be fully extended to all edges of the platen to make sure thickness is measured at 0.009 psi (6.32 g/cm²), except for the case of more rigid samples which are not flat. For more rigid samples which are not completely flat, a flat edge of the sample is measured using only one portion of the platen impinging on the flat portion of the sample. In the case of cylindrical, spherical, or other objects with more of a third dimension versus a pad or strip, the thickness is taken as the maximum distance of the shortest dimension, i.e., the diameter of a sphere or cylinder for instance, and the thickness ranges are the same as described above.

Shear Viscosity Test Method

The shear viscosity of the processing mixture of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A sample of the processing mixture, weighing 60 g and preheated to die test temperature (75° C.), is loaded into the barrel section of the rheometer. Any entrapped air is removed from the sample. Push the sample from the barrel through the capillary die at a set of chosen rates 1,000-10,000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta = K\gamma^{n-1}$, wherein K is the material's viscosity constant, n is the material's thinning index and $\gamma$ is the shear rate. The reported apparent shear viscosity of the composition herein is calculated from an interpolation to a shear rate of 3,000 sec$^{-1}$ using the power law relation.

Filament Composition Test Method

In order to prepare filaments for filament composition measurement, the coating composition, if any, must be removed from the filaments. The filaments are then air dried at 73° F. until the filaments comprise less than 10% moisture. A chemical analysis of the conditioned filaments is then completed to determine the compositional make-up of the filaments with respect to the backbone materials and the active agents and the level of the backbone materials and active agents present in the filaments.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, i.e., wt/wt percentages, unless otherwise specified.

Example 1

The following personal health care article can be prepared in accordance with the present invention:

| Component | Wt % of Processing Mixture |
|---|---|
| Ethylex 2035 Starch[1] | 32.13% |
| Naproxen-Na | 9.64% |
| Polyox WSR N-60K PEO[2] | 0.07% |
| Distilled Water | q.s. |
| Total | 100% |

[1]Ethylex ™ 2035 Starch available from Tate & Lyle (London, United Kingdom)
[2]Polyox ® WSR N-60K PEO available from Dow (Midland, Michigan)

Example 1 can be made by the following procedure. The distilled water is put into an appropriately sized and cleaned vessel and then is stirred at 100-300 revolutions per minute (rpm) and heated to 80° C. The Ethylex™ 2035 and Polyox® are weighed into a suitable container and are slowly added to the heated distilled water in small increments using a spatula. The Ethylex™ 2035 and Polyox® are added to the distilled water and continuously stirred at 80° C. until the Ethylex™ 2035 and Polyox® are dissolved resulting in the filament-forming mixture.

The filament-forming mixture is cooled to 25° C., then the naproxen-Na is slowly added to the filament-forming mixture and continuously stirred until the naproxen-Na is dissolved. The filament-forming mixture with the dissolved naproxen-Na is the processing mixture.

This processing mixture is made into filaments by meltblowing as described herein. Then, nonwoven webs are formed. The nonwoven webs will have a basis weight of about 600 g/m² and are then cut into personal health care articles with a surface area of about 8 cm². A mammal in need of a health benefit or a treatment for a health condition, can consume two personal health care articles, containing a total of about 220 mg naproxen-Na, by placing the articles directly into his or her mouth, allowing the personal health care article to disintegrate, and then swallowing the disintegrated article.

In the foregoing example, naproxen-Na can be replaced with an equivalent amount of phenylephrine HCl, diphenhydramine HCl, ranitidine HCl, vitamin B₉, and combinations thereof.

Example 2

The following personal health care article can be prepared in accordance with the present invention:

| Component | Wt % of Processing Mixture |
| --- | --- |
| Celvol 523 Polyvinyl Alcohol³ | 19.56% |
| Doxylamine Succinate | 4.46% |
| FD & C Blue #1 | 0.09% |
| Sucrose | 2.13% |
| Distilled Water | q.s. |
| Total | 100% |

³Celvol ® 523 available from Sekisui Corporation (Dallas, Texas)

Example 2 can be made by the following procedure. The distilled water is put into an appropriately sized and cleaned vessel and then is stirred at 100-300 rpm and heated to 80° C. The Celvol® 523 is weighed into a suitable container and is slowly added to the heated distilled water in small increments using a spatula. The Celvol® 523 is gradually added to the distilled water and continuously stirred at 80° C. until the Celvol® is dissolved resulting in the filament-forming mixture.

Then, the sucrose and blue #1 are slowly added to the filament-forming mixture. The temperature of the filament-forming mixture with the sucrose and blue #1 is maintained at 80° C. and continuously stirred until the sucrose and blue #1 are dissolved. The filament-forming mixture with sucrose and blue #1 is allowed to cool to 25° C., then the doxylamine succinate is slowly added while continuously stirring until the doxylamine succinate is dissolved to form the processing mixture.

This processing mixture is made into filaments by meltblowing as described herein. Then, nonwoven webs are formed and have a basis weight of about 92 g/m² and then cut into personal health care articles with a surface area of about 4 cm². A mammal in need of a health benefit or a treatment for a health condition, can consume one personal health care article, containing about 6.25 mg doxylamine succinate, by placing the articles directly into his or her mouth, allowing the personal health care article to disintegrate, and then swallowing the disintegrated article.

Example 3

The following personal health care article can be prepared in accordance with the present invention:

| Component | Wt % of Processing Mixture |
| --- | --- |
| Celvol 523 Polyvinyl Alcohol | 12.64% |
| Naproxen-Na | 13.83% |
| Doxylamine Succinate | 0.39% |
| Vanilla | 1.10% |
| Dextromethorphan HBr | 0.94% |
| Propylene Glycol | 10.11% |
| Distilled Water | q.s. |
| Total | 100% |

Example 3 can be made by the following procedure. The propylene glycol is put into an appropriately sized and cleaned vessel and then is stirred at 100-300 rpm at 25° C. The dextromethorphan HBr is weighed into a suitable container and is slowly added to the propylene glycol in small increments using a spatula. The propylene glycol and dextromethorphan HBr are stirred continuously at 100-300 rpm at 25° C. until the dextromethorphan HBr dissolves. The propylene glycol/dextromethorphan HBr mixture is set aside.

In a separate vessel, the distilled water is put into an appropriately sized and cleaned vessel and then is stirred at 100-300 rpm and heated to 80° C. The Celvol® 523 is weighed into a suitable container and is slowly added to the heated distilled water in small increments using a spatula. The Celvol® 523 is gradually added to the distilled water and continuously stirred at 80° C. until the Celvol® is dissolved resulting in the filament-forming mixture.

The filament-forming mixture is allowed to cool to 25° C., then the naproxen-Na/doxylamine succinate/vanilla mixture is slowly added to the filament-forming mixture and continuously stirred until the naproxen-Na, doxylamine succinate, and vanilla are dissolved. Then, the propylene glycol/dextromethorphan HBr mixture is added to the polyvinyl alcohol/naproxen-Na/doxylamine succinate/vanilla mixture at 25° C. The two mixtures are continuously stirred until the two mixtures have been uniformly blended to form the processing mixture.

This processing mixture is made into filaments by meltblowing as described herein. Then, nonwoven webs are formed that have a basis weight of about 390 g/m² and then cut into articles with a surface area of about 8 cm². A mammal in need of a health benefit or a treatment for a health condition, can consume two personal health care articles, containing a total of about 220 mg naproxen-Na, about 6.25 mg doxylamine succinate, and about 15 mg dextromethorphan, by placing the articles directly into his or her mouth, allowing the personal health care article to disintegrate, and then swallowing the disintegrated article.

Example 4

The following personal health care article can be prepared in accordance with the present invention:

| Component | Wt % of Processing Mixture |
|---|---|
| Ethylex 2035 Starch | 4.34% |
| Celvol 523 Polyvinyl Alcohol | 12.49% |
| Naproxen-Na | 19.54% |
| Vanilla | 0.54% |
| FD & C blue #1 | 0.11% |
| Sucrose | 1.63% |
| Distilled Water | q.s. |
| Total | 100% |

Example 4 can be made by the following procedure. The distilled water is put into an appropriately sized and cleaned vessel and then is stirred at 100-300 rpm and is heated to 80° C. The Celvol® 523 is weighed into a suitable container and is slowly added to the heated distilled water in small increments using a spatula while the distilled water is stirred continuously and forming visible lumps is avoided. The mixing speed is continuously adjusted to minimize foam formation. Once the Celvol® 523 is dissolved the Ethylex™ 2035 is weighed into a suitable container and is slowly added to the distilled water and Celvol® 523 mixture, in small increments using a spatula. The Celvol® 523 and Ethylex™ are added to the distilled water and continuously stirred at 80° C. until the Celvol® and Ethylex™ are dissolved resulting in the filament-forming mixture.

Then the naproxen-Na, vanilla, blue #1, and sucrose are slowly added to the filament-forming mixture and continuously stirred at 80° C. until the naproxen-Na, vanilla, blue #1, and sucrose are dissolved to form the processing mixture.

This processing mixture is made into filaments by melt-blowing as described herein. Then, nonwoven webs are formed with a basis weight of about 272 g/m² and then cut into personal health care articles with a surface area of about 8 cm². A mammal in need of a health benefit or a treatment for a health condition, can consume two personal health care articles, containing a total of 220 mg naproxen-Na, by placing the articles directly into his or her mouth, allowing the personal health care article to disintegrate, and then swallowing the disintegrated article.

In the foregoing example, naproxen-Na can be replaced with an equivalent amount of phenylephrine HCl, diphenhydramine HCl, ranitidine HCl, vitamin $B_9$, and combinations thereof.

Example 5

The following personal health care article can be prepared in accordance with the present invention:

| Component | Wt % of Processing Mixture |
|---|---|
| Celvol 523 Polyvinyl Alcohol | 13.53% |
| Naproxen-Na | 17.65% |
| Distilled Water | q.s. |
| Total | 100% |

Example 5 can be made by the following procedure. The distilled water is put into an appropriately sized and cleaned vessel and then is stirred at 100-300 rpm and heated to 80° C. The Celvol® 523 is weighed into a suitable container and is slowly added to the heated distilled water in small increments using a spatula. The Celvol® 523 is gradually added to the distilled water and continuously stirred at 80° C. until the Celvol® is dissolved resulting in the filament-forming mixture.

The filament-forming mixture is allowed to cool to 25° C. and then the naproxen-Na is slowly added and stirred continuously until the naproxen-Na is dissolved resulting in the processing mixture.

The processing mixture is made into filaments by melt-blowing as described herein. Then, nonwoven webs are formed and have a basis weight of about 243 g/m² and then cut into personal health care articles with a surface area of about 8 cm². A mammal in need of a health benefit or a treatment for a health condition, can consume two personal health care articles, containing about 220 mg of naproxen-Na, by placing the articles directly into his or her mouth, allowing the personal health care article to disintegrate, and then swallowing the disintegrated article. Alternatively two personal health care articles can be placed into 8 ounces of water, stirred until dissolved, and then drank by a mammal in need to deliver about 220 mg of naproxen-Na.

Example 6

The following personal health care article can be prepared in accordance with the present invention:

| Component | Wt % of Processing Mixture |
|---|---|
| Celvol 523 Polyvinyl Alcohol | 13.53% |
| Naproxen-Na | 17.65% |
| Distilled Water | q.s. |
| Total | 100% |

Example 6 can be made according to the procedure in Example 5 except after the nonwoven webs are cut into personal health care articles the surface of the personal health care article is lightly brushed with distilled water Immediately following, 120 mg of pseudoephedrine HCl is applied to the wetted surface. Then personal health care article is formed by allowing the coating is to dry at 25° C. for 16 hours in a desiccator that is protected from light.

A mammal in need of a health benefit or a treatment for a health condition, can consume one personal health care article, containing about 220 mg of naproxen-Na and about 120 mg of pseudoephedrine, by placing the article directly into his or her mouth, allowing the personal health care article to disintegrate, and then swallowing the disintegrated article.

Example 7

The following personal health care article can be prepared in accordance with the present invention:

| Component | Wt % of Processing Mixture |
| --- | --- |
| Isomalt (Smart Sweet ™ Granules)[4] | 67% |
| Retail Cold & Flu Product[5] (Vicks ® NyQuil ® Cold & Flu (Cherry Flavor)) | 7.58% |
| Distilled Water | q.s. |
| Total | 100% |

[4]Smart Sweet™ Granules are available from Global Sweet Polyols (Rehoboth, Massachusetts)
[5]Vicks ® NyQuil ® Less Drowsy Cold & Flu (Cherry Flavor) is available from The Procter & Gamble Company (Cincinnati, Ohio)

Example 7 can be made by the following procedure. The distilled water is put into an appropriately sized and cleaned vessel and then is stirred at 100-300 rpm and heated to 25° C. The retail cold and flu product is measured and slowly added to the distilled water.

In a separate container, the isomalt granules are weighed into a suitable container and are slowly heated to 150° C. until the isomalt granules are melted. Then, the retail cold and flu/distilled water mixture is gradually added to the melted isomalt and continuously stirred at 150° C. until the retail cold and flu/distilled water mixture is fully incorporated into the melted isomal to form the processing mixture.

The processing mixture is made into filaments by fluid film fibrillation as described herein.

Then, nonwoven webs are formed and then the nonwoven webs are cut into personal health care articles with a surface area of about 8 cm².

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care article comprising:
   a. a first nonwoven web and a second nonwoven web, the first nonwoven web and the second nonwoven web each comprising:
      i. from about 10% to about 80%, by weight of the respective nonwoven web, of one or more backbone materials, and
      ii. less than 10%, by weight of the respective nonwoven web, of water; and
   b. a coating composition sealed between the first nonwoven web and the second nonwoven web, the coating composition comprising bleaching agent;
   wherein the coating composition is releasable from the oral care article upon exposure to an oral cavity.

2. The oral care article of claim 1, wherein the first and second nonwoven web comprise from about 10% to about 70%, by weight of the respective nonwoven web, of surfactant.

3. The oral care article of claim 2, wherein the surfactant comprises anionic surfactant, zwitterionic surfactant, or a combination thereof.

4. The oral care article of claim 2, wherein the surfactant comprises alkyl sulfate and betaine compound.

5. The oral care article of claim 1, wherein the one or more backbone materials comprises a synthetic polymer, a sugar alcohol, or a combination thereof.

6. The oral care article of claim 5, wherein the one or more backbone materials comprises the synthetic polymer, and the synthetic polymer comprises polyvinyl alcohol.

7. The oral care article of claim 6, wherein the one or more backbone materials further comprises the sugar alcohol, and the sugar alcohol is xylitol.

8. The oral care article of claim 1, wherein the oral care article comprises an aesthetic agent.

9. The oral care article of claim 8, wherein the aesthetic agent comprises flavors, sensates, sweeteners, salivation agents, or combinations thereof.

10. The oral care article of claim 1, wherein the first and second nonwoven webs comprise a meltblown filament.

11. The oral care article of claim 10, wherein the meltblown filament has a basis weight of from about 20 g/m² to about 1000 g/m².

12. The oral care article of claim 1, wherein the bleaching agent comprises hydrogen peroxide, perborate, percarbonate, or combinations thereof.

13. An oral care article comprising:
   a. a nonwoven web, the nonwoven web comprising:
      i. from about 10% to about 80%, by weight of the nonwoven web, of one or more backbone materials, and
      ii. less than 10%, by weight of the nonwoven web, of water,
      wherein the nonwoven web is folded to form a pouch; and
   b. a coating composition sealed within the pouch, the coating composition comprising bleaching agent;
   wherein the coating composition is releasable from the oral care article upon exposure to an oral cavity.

14. The oral care article of claim 13, wherein the nonwoven web comprises from about 10% to about 70%, by weight of the nonwoven web, of surfactant.

15. The oral care article of claim 14, wherein the surfactant comprises anionic surfactant, zwitterionic surfactant, or a combination thereof.

16. The oral care article of claim 15, wherein the surfactant comprises alkyl sulfate and betaine compound.

17. The oral care article of claim 13, wherein the one or more backbone materials comprises a synthetic polymer, a sugar alcohol, or a combination thereof.

18. The oral care article of claim 17, wherein the one or more backbone materials comprises the synthetic polymer, and the synthetic polymer comprises polyvinyl alcohol.

19. The oral care article of claim 18, wherein the one or more backbone materials further comprises the sugar alcohol, and the sugar alcohol is xylitol.

20. The oral care article of claim 13, wherein the oral care article comprises an aesthetic agent.

21. The oral care article of claim 20, wherein the aesthetic agent comprises flavors, sensates, sweeteners, salivation agents, or combinations thereof.

22. The oral care article of claim 1, wherein the nonwoven web comprises a meltblown filament.

23. The oral care article of claim 22, wherein the meltblown filament has a basis weight of from about 20 $g/m^2$ to about 1000 $g/m^2$.

24. The oral care article of claim 13, wherein the bleaching agent comprises hydrogen peroxide, perborate, percarbonate, or combinations thereof.

\* \* \* \* \*